(12) United States Patent
Liu et al.

(10) Patent No.: US 9,983,399 B2
(45) Date of Patent: May 29, 2018

(54) DEPTH-RESOLVED SPATIAL-DOMAIN LOW-COHERENCE QUANTITATIVE PHASE MICROSCOPY FOR UNSTAINED TISSUE AND CELLS

(71) Applicant: University of Pittsburgh—Of the Commonwealth System of Higher Education, Pittsburgh, PA (US)

(72) Inventors: Yang Liu, Sewickley, PA (US); Hoa Vinh Pham, Pittsburgh, PA (US); Shikhar Fnu, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 132 days.

(21) Appl. No.: 15/055,222

(22) Filed: Feb. 26, 2016

(65) Prior Publication Data
US 2016/0252719 A1 Sep. 1, 2016

Related U.S. Application Data

(60) Provisional application No. 62/126,293, filed on Feb. 27, 2015.

(51) Int. Cl.
*G06K 9/00* (2006.01)
*G02B 21/36* (2006.01)
(Continued)

(52) U.S. Cl.
CPC ....... *G02B 21/367* (2013.01); *G01N 33/4833* (2013.01); *G02B 21/0056* (2013.01);
(Continued)

(58) Field of Classification Search
CPC .. G02B 21/367; G02B 21/0056; G02B 21/12; G02B 21/14; G06T 7/337;
(Continued)

(56) References Cited

U.S. PATENT DOCUMENTS 6,259,807 B1 7/2001 Ravkin
8,320,650 B2 * 11/2012 Demos ................. A61B 5/0071
356/51

(Continued)

OTHER PUBLICATIONS

Liu et al.: "Investigation of nanoscale structural alterations of cell nucleus as an early sign of cancer," BMC Biophysics 2014, 7:1.

(Continued)

*Primary Examiner* — Shefali Goradia
(74) *Attorney, Agent, or Firm* — Eckert Seamans Cherin & Mellott, LLC; Philip E. Levy

(57) ABSTRACT

Provided are systems, methods, and other embodiments associated with depth-resolved spatial-domain low-coherence quantitative phase microscopy for high-throughput analysis of 3D nanoscale architectural alterations in unstained tissue and cells. A spatial-domain low-coherence quantitative phase microscopy apparatus includes a drOPD mapping module, a transmission phase imaging module, and a bright-field and transmission phase imaging module. The drOPD mapping module includes a reflection-mode low-coherence spectral interferometry for drOPD mapping of unstained tissue. The transmission phase imaging module includes transmission quantitative phase imaging of unstained and stained tissue and produce an image registration reference. The bright-field and transmission phase imaging module includes bright-field imaging of H&E-stained tissue for nuclei identification and pathology correlation.

19 Claims, 21 Drawing Sheets

(51) Int. Cl.
  *G01N 33/483* (2006.01)
  *G02B 21/12* (2006.01)
  *G02B 21/14* (2006.01)
  *H04N 13/00* (2018.01)
  *G02B 21/00* (2006.01)
  *G06T 7/33* (2017.01)

(52) U.S. Cl.
  CPC .............. *G02B 21/12* (2013.01); *G02B 21/14* (2013.01); *G06T 7/337* (2017.01); *H04N 13/0022* (2013.01); *G06T 2207/10028* (2013.01); *G06T 2207/10056* (2013.01); *G06T 2207/30024* (2013.01)

(58) Field of Classification Search
  CPC . G06T 2207/10028; G06T 2207/10056; G06T 2207/30024; G01N 33/4833; H04N 13/0022
  See application file for complete search history.

(56) References Cited

U.S. PATENT DOCUMENTS

| | | | |
|---|---|---|---|
| 2014/0350395 A1 | 11/2014 | Shachaf et al. | |
| 2015/0204728 A1* | 7/2015 | Liu | G01J 9/02 356/497 |
| 2015/0374451 A1* | 12/2015 | Kim | A61B 1/00009 600/424 |

OTHER PUBLICATIONS

Hoa V. Pham et al., "Multimodal hyperspectral full-field quantitative phase microscopy," Biomedical Optics 2014, OSA online journal.

* cited by examiner

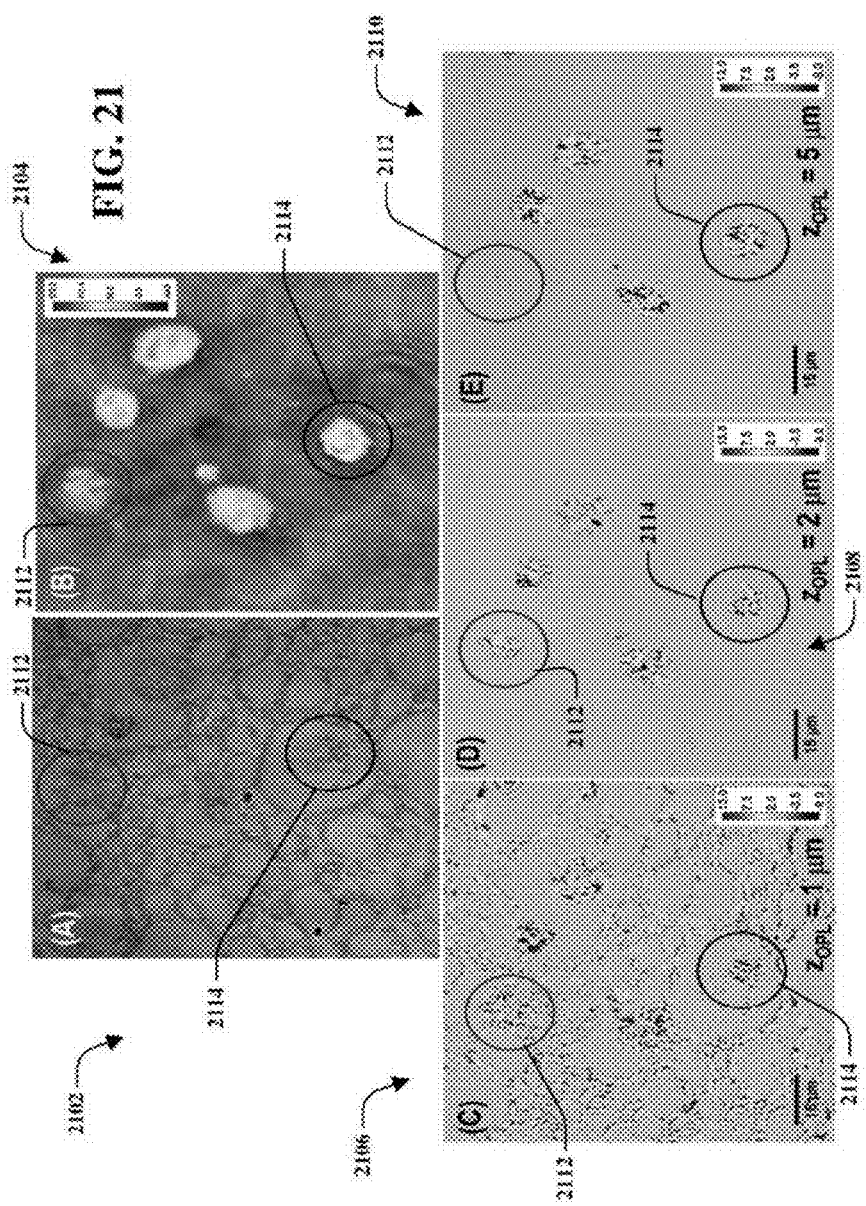

DEPTH-RESOLVED SPATIAL-DOMAIN LOW-COHERENCE QUANTITATIVE PHASE MICROSCOPY FOR UNSTAINED TISSUE AND CELLS

CROSS REFERENCE

This application claims the benefit of U.S. Provisional Application Ser. No. 62/126,293, filed on Feb. 27, 2015, and entitled "DEPTH-RESOLVED SPATIAL-DOMAIN LOW-COHERENCE QUANTITATIVE PHASE MICROSCOPY FOR HIGH-THROUGHPUT ANALYSIS OF 3D NANOSCALE ARCHITECTURAL ALTERATIONS IN UNSTAINED TISSUE AND CELLS", the entirety of which is expressly incorporated herein by reference.

NOTICE ON GOVERNMENT FUNDING

This invention was made with government support under grants R01EB016657 and R01CA185363 awarded by the National Institute of Health. The government has certain rights in the invention.

BACKGROUND

Early cancer detection currently relies on screening the entire at-risk population, such as with colonoscopy and mammography. Thus, frequent and invasive surveillance of patients at risk for developing cancer carries financial, physical, and emotional burdens because clinicians lack tools to accurately predict which patients will actually progress into malignancy.

Cancer develops through a series of genetic and epigenetic events that result in architectural changes in the cell nucleus. As such, alteration in nuclear architecture has been the gold standard in pathology for cancer diagnosis and prognosis. Given that nuclear architecture is conventionally assessed at the two-dimensional (2D) microscopic images (e.g., approximately 500 nm resolution) of tissue sections stained with hemotoxylin and eosin, the characteristic morphological changes identified in cancerous or precancerous cells are limited to mostly micron-scale features, and are considered to be a late manifestation of carcinogenesis. These features include increased nuclear size, irregular nuclear shape, and coarse chromatin texture. Many structural abnormalities observable at the micro-scale do not occur until an advanced stage, making it difficult to distinguish early-stage cancers from benign conditions.

Further, the detection of pre-cancer or early-stage cancer is not sufficient in many clinical settings. As many pre-cancers or early-stage cancers will never progress into invasive cancer, detection may lead to unnecessary treatment in the absence of aggressive cancer. This unnecessary treatment may do more harm than good to the patient at a high cost. Therefore, it is important to not only identify pre-cancer or early-stage cancer, but also predict which pre-cancer or early-stage cancer is likely to develop into a more invasive form (e.g., prognosis). This microscale nuclear morphology has some prognostic value, but its accuracy is somewhat limited. For higher accuracy and sensitivity in cancer diagnosis and prognosis, there is an urgent need for new methods and systems to assess nuclear architectural changes at the nanoscale, well beyond micron-scale features, with a high throughput that is clinically applicable.

Due to the advancement in understanding cancer genome and epigenome, it is now recognized that the genome function is not just regulated by the linear sequence of DNA, and the spatial organization of chromatin plays a key role in cancer development. The detection of whole-genome level 3D spatial distribution of chromatin at a single cell nucleus level in clinically prepared samples seems to be an astonishing task. On the other hand, the detection of the changes in the 3D spatial arrangement and the chromatin density variation in the cell nucleus as the downstream structural changes of complex genomic and epigenomic changes in carcinogenesis may have potential as a high throughput approach.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The various aspects discussed herein provide depth-resolved spatial-domain low-coherence quantitative phase microscopy for high-throughput analysis of 3D nanoscale architectural alterations in unstained tissue and cells. An aspect relates to a spatial-domain low-coherence quantitative phase microscopy apparatus. The apparatus includes an imaging system that collimates a white light from a light source and a component that tunes a wavelength of the white light to a spectral resolution shared by multiple imaging contrasts. The apparatus also includes a device that projects the tuned light onto a sample, wherein the sample scatters at least a portion of the tuned light back. Further, the apparatus includes a camera that records the scattered portion of the tuned light and an image registration module that co-registers images.

Another aspect relates to a spatial-domain low-coherence quantitative phase microscopy method that includes tuning a wavelength of a white light and projecting the tuned light onto a sample. The sample scatters at least a portion of the tuned light back. The method also includes recording the scattered portion of the tuned light with a camera and generating depth-resolved three-dimensional images based, at least in part, on a measurement of the scattered portion. Further, the method includes auto-focusing the depth-resolved three-dimensional images based, at least in part, on a fixed wavelength and co-registering the depth-resolved three-dimensional images.

A further aspect relates to a spatial-domain low-coherence quantitative phase microscopy apparatus that includes a drOPD mapping module comprising a reflection-mode common-path low-coherence spectral interferometry for drOPD mapping of unstained tissue. The apparatus also includes a transmission phase imaging module that includes transmission quantitative phase or phase contrast imaging of unstained and stained tissue and produces an image registration reference. Further, the apparatus includes a bright-field imaging module that includes bright-field imaging of H&E-stained tissue for nuclei identification and pathology correlation. In addition, the transmission phase imaging module further obtains a high-contrast transmission phase map for identifying overall tissue architecture of unstained tissue imaging module to produce the image registration reference.

To the accomplishment of the foregoing and related ends, certain illustrative aspects of the innovation are described herein in connection with the following description and the annexed drawings. These aspects are indicative, however, of but a few of the various ways in which the principles of the innovation may be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

Various non-limiting embodiments are further described with reference to the accompanying drawings in which:

FIG. 21 illustrates a demonstration of depth-resolved capability of depth resolved optical path-length difference imaging.

DETAILED DESCRIPTION

Figure 1:
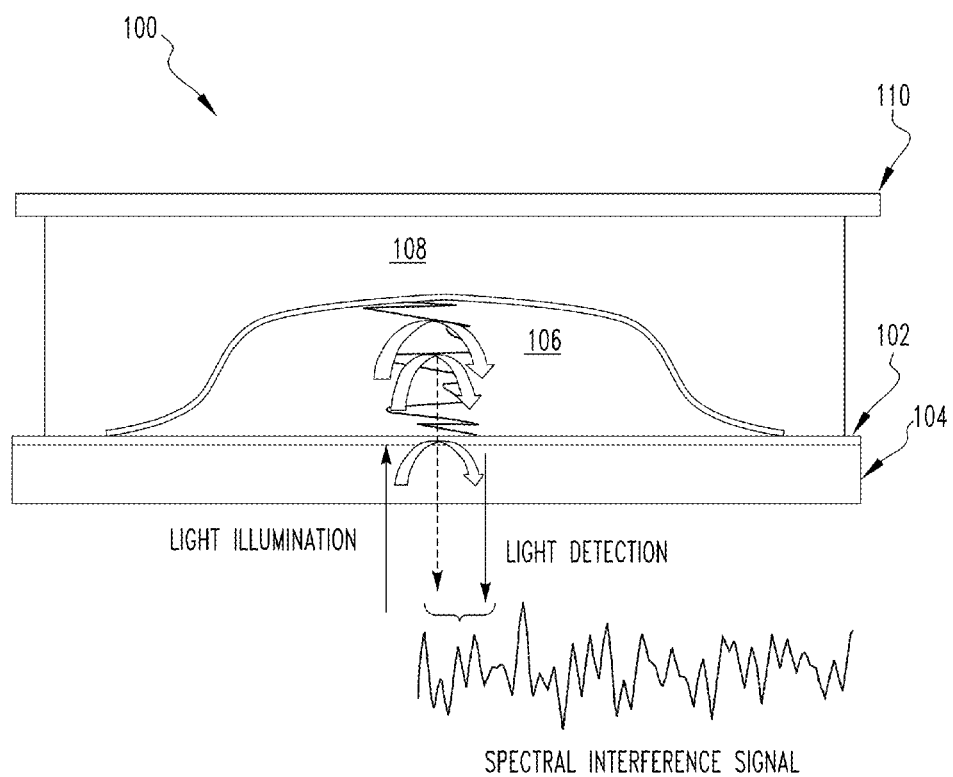
FIG. 1 illustrates an example, non-limiting embodiment of a slide configuration associated with depth-resolved spatial-domain low-coherence quantitative phase microcopy for high-throughput analysis of 3D nanoscale architectural alterations in unstained tissue and cells, according to an aspect.

The innovation is now described with reference to the drawings. In the following description, for purposes of explanation, numerous specific details are set forth in order to provide a thorough understanding of the subject innovation. It may be evident, however, that the innovation may be practiced without these specific details. In other instances, well-known structures and devices are shown in block diagram form in order to facilitate describing the innovation.

A challenge for early cancer detection is how to effectively manage patients who are at risk for developing invasive cancer, such as patients with ulcerative colitis or those with precancerous lesions. Most at-risk patients will not develop cancer and do not warrant treatment or frequent surveillance. Without an accurate means to assess which at-risk patients are likely to progress into malignancy at an early stage of cancer development prior to the detection of clinically significant lesions, clinicians and patients may opt to pursue additional invasive procedures for surveillance or treatment. Conversely, a more conservative approach could miss the opportunity to address cancer at an early stage.

Cancer arises mostly from accumulation of somatic mutations, which are further regulated by epigenetic changes that transform normal cells into malignant form. Nuclear architecture, organized into condensed and open compartments, plays a role in regulating the function of genome and epigenome during cancer progression. A clinical gold standard for diagnosing cancer and predicting cancer progression risk relies on the evaluation of morphologic features of stained tissue slide from formalin-fixed, paraffin-embedded (FFPE) tissue section by a trained pathologist using a bright-field microscope. The visible microscopic changes in cell nuclei are based on spatial distribution of light absorbance by DNA-binding dyes, such as hematoxylin and Feulgen stains. For example, coarse aggregation of condensed chromatin, hyperchromasia, and nuclear pleomorphism are among the established nuclear architecture characteristics of cancer cells. Despite its clinical significance, traditional microscopic nuclear architecture does not provide enough sensitivity to predict cancer progression risk on a personalized level. Some approaches to assess nuclear architecture use nuclear stains as a surrogate marker, and their ability to reflect the underlying architecture depends on the affinity of the dye and its chemical interaction with the nuclear component. However, subtle changes in nuclear density may not be detectable with a traditional light microscopy.

Disclosed herein are systems and methods to image nuclear architecture on unstained tissue by quantifying the intrinsic depth-resolved density alteration of nuclear architecture, referred to as nanoscale nuclear architecture mapping (nanoNAM). The image resolution of a nuclear architecture map may be diffraction-limited, but the image contrast with nanoscale precision is produced by depth resolved optical path-length difference (drOPD) arising from the alteration of three-dimensional refractive index profile within the nucleus. A refined nanoNAM that can be used with standard unstained deparaffinized tissue slide made from FFPE tissue block that removes the effect of variations in clinical sample preparation, such as tissue section thickness and staining, is provided herein.

According to various experiments discussed herein involving animals and humans, nanoNAM was first applied to unstained tissue slide from an animal model in which cancer is induced by inflammation agent and carcinogen. To evaluate the clinical utility of nanoNAM, tissue from patients with ulcerative colitis were examined. Ulcerative colitis is a disease characterized by chronic colonic inflammation and carries increased risk for high-grade dysplasia (HGD) and colorectal adenocarcinoma. Clinical guidelines currently recommend that these patients undergo annual or biennial colonoscopy with 4-quadrant biopsies every 10 cm throughout the involved colon. Therefore, a tool to better distinguish those at genuine risk for cancer from those in whom surveillance could be relaxed would improve outcome, cost effectiveness, and the patient's quality of life. The various aspects discussed herein provide techniques for mapping nuclear architecture at a nanoscale sensitivity and present results in animal and human tissue.

The depth-resolved nanoscale nuclear architecture mapping (nanoNAM) is a derivative of spectral-domain optical coherence tomography. It has been shown that the phase, rather than the amplitude, of a Fourier-transformed spectral interference signal captures the subresolution structural changes in an optical path length at a strong interface of interest, where the refractive index between the tissue and the surrounding medium has a strong mismatch. However, when analyzing nuclear architecture from FFPE tissue section, such nanoscale sensitivity is often compromised because the tissue section thickness cannot be controlled with a nanometer precision. As discussed herein, this limitation is overcome by constructing a tissue slide with closely matched refractive index between the tissue and mounting medium. In the absence of a strong interface, the phase of Fourier-transformed spectral inference signals at each of the predefined optical-depth locations quantifies nanoscale structural characteristics within the coherence-gated optical-depth location, referred to as depth-resolved OPD (drOPD). The mathematical expression of spectral interference signals for drOPD mapping will be provided later in this detailed description To enable drOPD imaging on the glass slide-based tissue samples, a reflection-mode low-coherence common-path spectral interferometer may be built upon the glass slide-based sample itself. FIG. 1 illustrates an example, non-limiting embodiment of a slide configuration 100 associated with depth-resolved spatial-domain low-coherence quantitative phase microcopy for high-throughput analysis of 3D nanoscale architectural alterations in unstained tissue and cells, according to an aspect. Clinically prepared tissue or cells are weakly scattering samples. With the closely matched refractive index of the mounting medium, the scattered signals are fairly weak. To enhance the signal-to-noise ratio while minimizing the difference from standard clinical tissue processing, the glass slide in the configuration is provided as illustrated in FIG. 1.

A single-layer dielectric coating 102 (e.g., a reflection-enhancing coating) is added to a glass slide 104. A reflection from the single-layer dielectric coating 102 (e.g. approximately 20% reflection and about 80% transmission) on the standard glass slide 104 generates a stable reference wave. The reflection may also enhance signal-to-noise ratio for weakly scattered unstained samples.

A sample 106 (e.g., a tissue or cell section) is placed on the coated side of the slide, deparaffinized, and mounted with a mounting media 108 (e.g., Surgipath®, Leica, or the like) to match the refractive index of the sample and minimize the strong interface (or refractive index mismatch) between the sample 106 and the mounting media 108. The sample 106 may then be cover-slipped, as illustrated by the coverslip 110. The backscattered waves from the tissue (e.g., the sample 106), together with the reference waves, may be collected as a function of wavelengths (e.g., spectral interference signal).

According to some implementations, for spatial-domain low-coherence quantitative phase microscopy (SL-QPM) measurement, to maximize the collection of weak scattering signals, a right-angle prism may be applied on top of the coverslip 110 with immersion oil in between. This may help to ensure the strong reflection at the coverslip/air interface does not overwhelm the signals scattered from the sample.

By way of example and not limitation, the following is a sample preparation for nanoNAM that may be utilized with the disclosed aspects. First, an unstained slide from a recut from FFPE tissue block is prepared. The FFPE tissue block may be sectioned at 5 μm thickness using a microtome, which is placed on the coated glass slide as described above. Then the tissue is deparaffinized, rehydrated in ethanol series with graded alcohol (about 100%, 95%, 70% and 50%) and then dehydrated back to xylene in the reverse order. The unstained slide is then coverslipped with mounting medium (e.g., Micromount®, n=1.50 for dried mounting medium, Surgipath®, Leica).

After drOPD mapping and transmission phase imaging on the unstained tissue, the slide is immersed in xylene overnight (or a similar period of time) to remove the coverslip. The de-coverslipped tissue slide is then rehydrated in ethanol series with graded alcohol (the same as (or similar to) the processing for unstained slide), stained with hematoxylin and eosin, and then dehydrated back to xylene in reverse order of grade alcohol. The slide is then coverslipped with the same mounting medium. The hematoxylin and eosin (H&E)-stained slide was imaged with bright-field and transmission phase microscopy for pathology correlation, nuclei segmentation and image registration.

Figure 2:
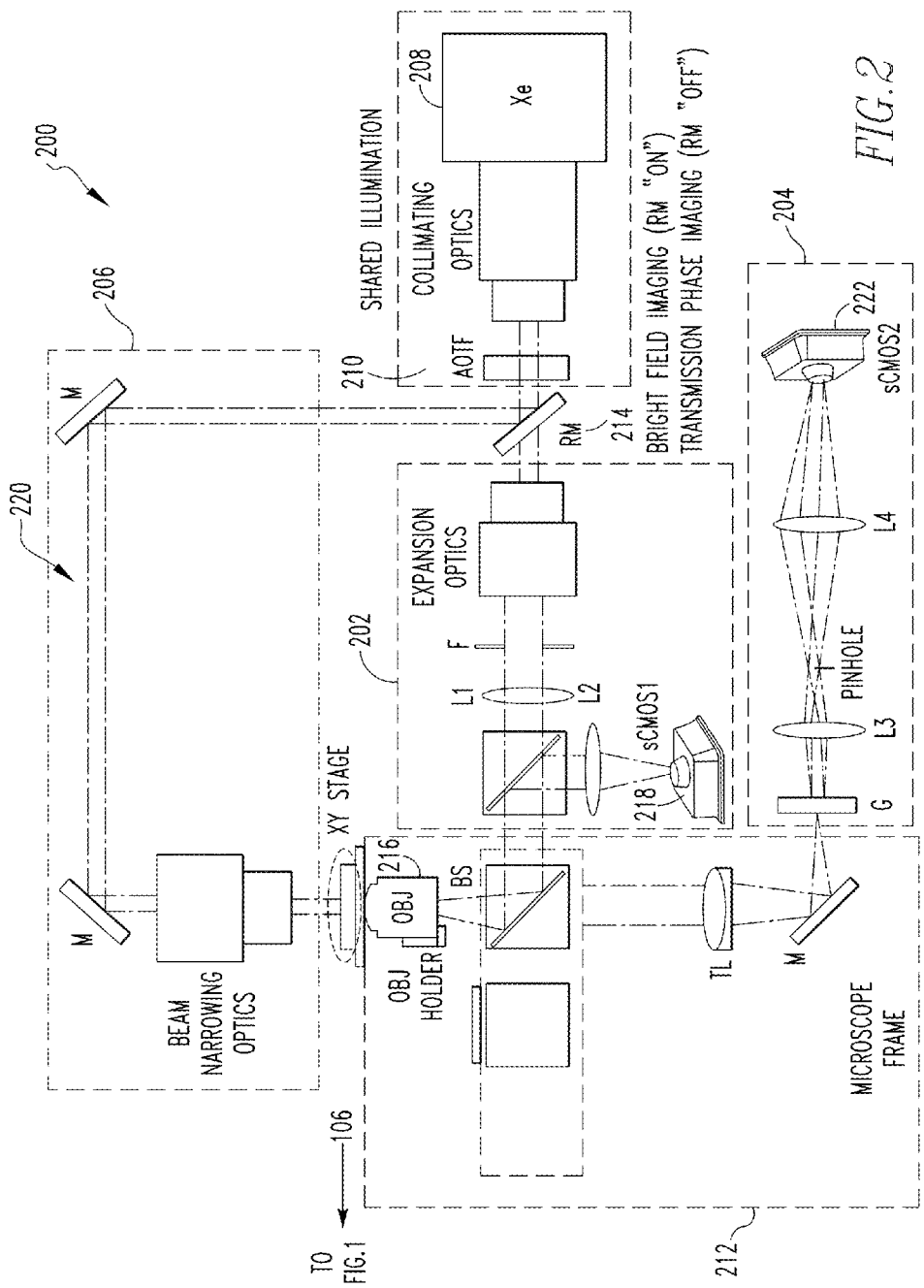
FIG. 2 illustrates an example, non-limiting optical microscopy system for nanoscale nuclear architecture mapping, according to an aspect.

FIG. 2 illustrates an example, non-limiting optical microscopy system 200 for nanoscale nuclear architecture mapping (nanoNAM), according to an aspect. Due to the lack of sufficient image contrast to reliably identify cell nuclei in drOPD and transmission phase images, the optical microscopy system 200 may include multiple imaging contrasts. According to an implementation, the multiple imaging contrasts may be three complementary imaging modules to utilize the strength of each for the entire task of nanoNAM. However, fewer or more than three imaging modules may be utilized with the disclosed aspects. These multiple imaging contrasts (e.g., modules) may include a drOPD mapping module 202, a transmission phase imaging module 204, and an illumination for bright-field imaging module 206.

The drOPD mapping module 202 may include a reflection-mode common-path low-coherence spectral interferometry for drOPD mapping of unstained tissue. The transmission phase imaging module 204 may include transmission quantitative phase imaging of unstained and stained (e.g., with hematoxylin and eosin (H&E)) tissue to obtain a high-contrast transmission phase map for identifying overall tissue architecture of unstained tissue, which also serves as an image registration reference. Further, the illumination optics for bright-field imaging module 206 may include bright-field imaging of H&E-stained tissue for nuclei identification and pathology correlation. Further details related to the operation of the optical microscopy system 200 will be provided below.

Figure 3:
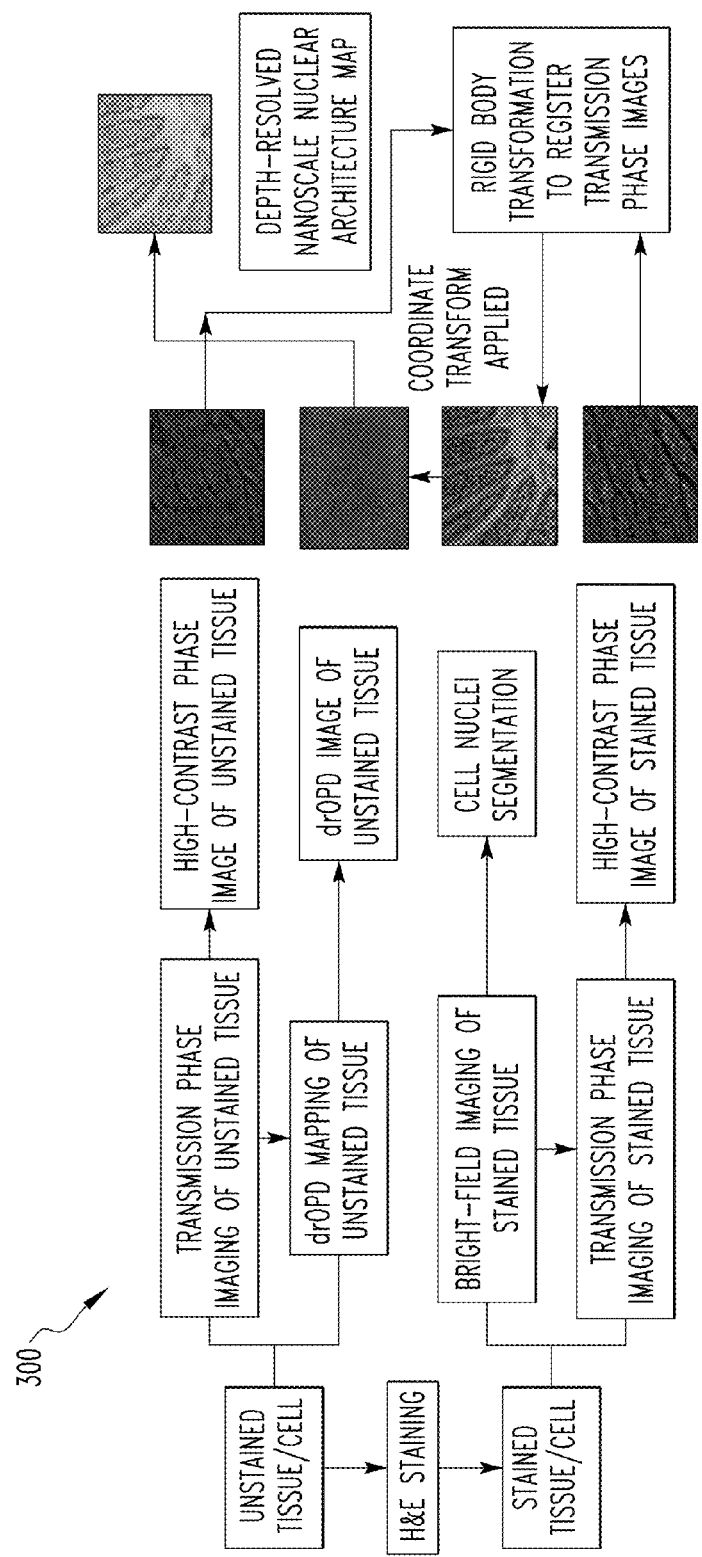
FIG. 3 illustrates an example, non-limiting method associated with depth-resolved spatial-domain low-coherence quantitative phase microscopy for high-throughput analysis of 3D nanoscale architectural alterations in unstained tissue and cells.

FIG. 3 illustrates an example, non-limiting method 300 associated with depth-resolved spatial-domain low-coherence quantitative phase microscopy for high-throughput analysis of 3D nanoscale architectural alterations in unstained tissue and cells. In FIG. 3, the depth-resolved nanoscale structural analysis and transmission phase measurement are first performed on unstained tissue slide, then the slide is stained with a standard hematoxylin and eosin (H&E) staining protocol for cell nucleus identification. Last, another transmission phase measurement is performed on the H&E stained slides. From the transmission phase measurement of unstained and stained tissue, the coordinate transformation matrix is extracted to register the unstained and stained images based on the method described below. Then this transformation matrix is applied to the bright-field image of stained sample to register all the segmented cell nuclei into the depth-resolved phase map of the unstained tissue.

The following will explain an example, non-limiting nanoNAM instrument setup, according to an aspect. With reference again to FIG. 2, a light source that produce a white light is provided. In an implementation, the light source may be a low-coherence white light Xenon lamp 208 (e.g., EQ-99, Energetiq, or another type of device) may be used. The white light is collimated and the collimated beam may be processed to tune the wavelength of the white light. According to an implementation, the collimated beam may be passed through a high-speed acousto-optical tunable filter (AOTF 210) to tune the wavelength (480-700 nm) at a spectral resolution of 1-3 nm, shared by the multiple imaging contrasts (e.g., the imaging modules). A standard microscope frame 212 (e.g., from AxioObserver, Carl Zeiss) may be used.

The light may be directed to a sample. According to an implementation, a flipping mirror (RM 214) may be used to direct the illumination into the different modules. When RM 214 is at an "off" position, the illumination beam is reflected by beam splitter (BS), and focused onto the back focal plane of the objective (OBJ 216) by achromatic lens L1 to achieve a uniform field of view (~250 µm diameter).

The reflected reference wave and backscattered light from the sample are collected with OBJ 216, achromatic lens (L2) and projected onto the camera sCMOS1 218 (e.g., pco.edge, PCO-TECH). To avoid double transmission (e.g., the reflected light at coverslip/air interface passing through the sample), a right-angle prism (e.g., Edmund Optics) was used on top of the coverslip with immersion oil (n=1.515) in between to deflect the light outside the microscope system.

The images at ~230 wavelengths tuned by AOTF 210 are recorded (e.g., using a processor and a memory) with a total of 20 seconds, repeated four times to average out the noise. The inter-user variation in identifying focal plane was removed via an automatic focusing method (which will be discussed further below and with reference to FIG. 4), with the objective mounted on an objective nano-positioner (e.g., Edmund Optics). Wavelength-dependent focal plane shift and image distortion was also corrected (as will be described in further detail below and with reference to FIG. 5 and FIG. 6).

Then RM 214 is placed at "on" position, the beam is used for trans-illumination (dashed line 220) for transmission phase imaging based on the configuration of diffraction phase microscope. At the image plane located at the side port of the microscope frame, a transmission grating G (e.g., Edmund Optics), is used to create different copies of the emerging field. At the back focal plane of the lens L3, the DC component filtered from the $0^{th}$-diffraction order and the entire $1^{st}$-order diffracted beam are collected and interfere on the camera sCMOS2 222 at a wavelength of ~560 nm.

After the unstained tissue is imaged, the slide is stained with H&E, which is then imaged with bright-field (collected by sCMOS1 218) and transmission phase modules (e.g., 202 and 204). The slide is mounted on a motorized high-precision translational stage (e.g., MLS203-2, Thorlabs) to record the same sets of locations before and after staining and for automatic lateral scanning of multiple areas. The transmission phase imaging module 204 can include any phase contrast imaging mechanism and is not limited to diffraction phase microscope. Similarly, the sensors used to image the drOPD, bright-field and phase contrast images are not limited to sCMOS.

The following is an example, non-limiting method for automatic focusing, according to an aspect. To ensure the consistency of focal plane position by different users, a simple derivative-based algorithm was utilized to perform autofocusing. At each image location, a fixed wavelength is chosen, and z-stack reflectance images are acquired. A squared gradient algorithm is then used to define the position of the focal plane. Specifically, at each image, the focus measure is calculated as $$F(z) = \sum_{height} \sum_{width} (I(x+1, y) - I(x, y))^2 + (I(x, y+1) - I(x, y))^2,$$

where $$\sum_{height} \sum_{width} (I(x+1, y) - I(x, y))^2 + (I(x, y+1) - I(x, y))^2 \geq \theta$$

and θ is the gradient threshold. Then, the focus plane is found by $$z_0 = \underset{z}{\mathrm{argmax}}(F(z)).$$

Figure 4:
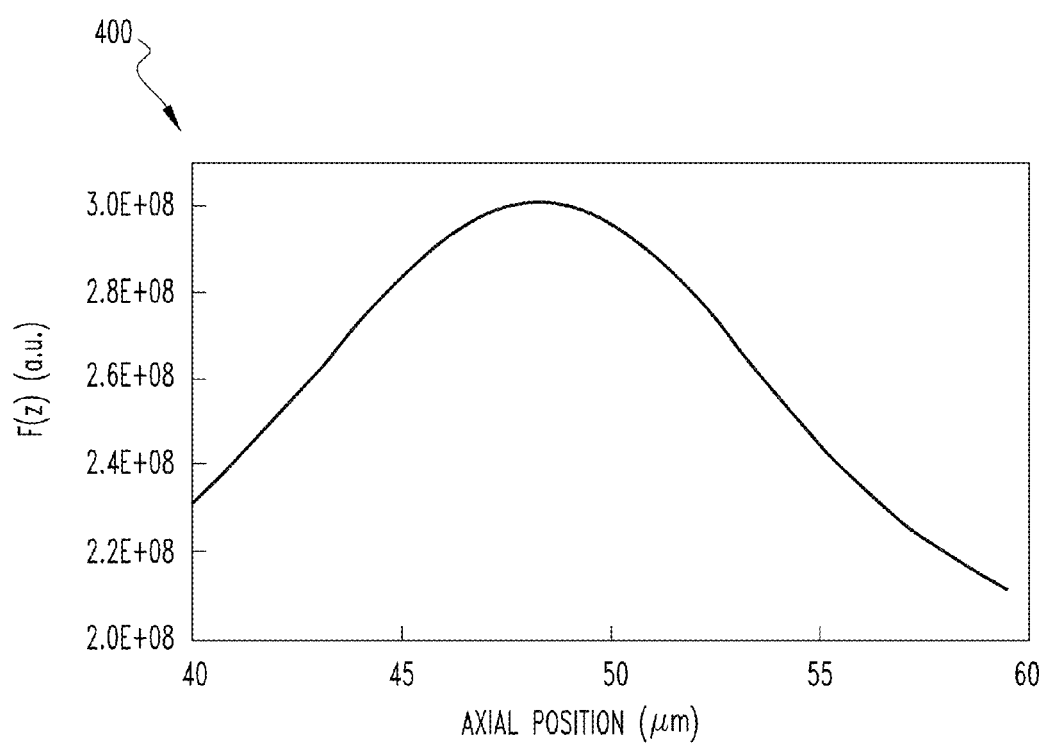
FIG. 4 illustrates an example, non-limiting squared gradient plot versus the axial position of objective lens at the wavelength of 50 nm.

FIG. 4 illustrates an example, non-limiting squared gradient plot 400 versus the axial position of objective lens at the wavelength of 560 nm. Illustrated is the focus measure F(z) as a function of focal plane position (z), and the focal plane is defined as the axial z position with the maximum value of F(z).

An example, non-limiting correction for wavelength-dependent focal plane shift will now be discussed. Despite the achromatic optics that are used throughout the entire optical system, the chromatic aberration is still present in the optical system with a small focal shift of several microns in the spectral range of 490-680 nm. In order to further correct for this chromatic aberration, a chromatic correction curve was developed. Specifically, 18 wavelengths (evenly spaced in the spectral range of 490 to 680 nm were used. For each wavelength, the above autofocusing algorithm was used to obtain the focal shift curve along the entire spectral range.

Figure 5:
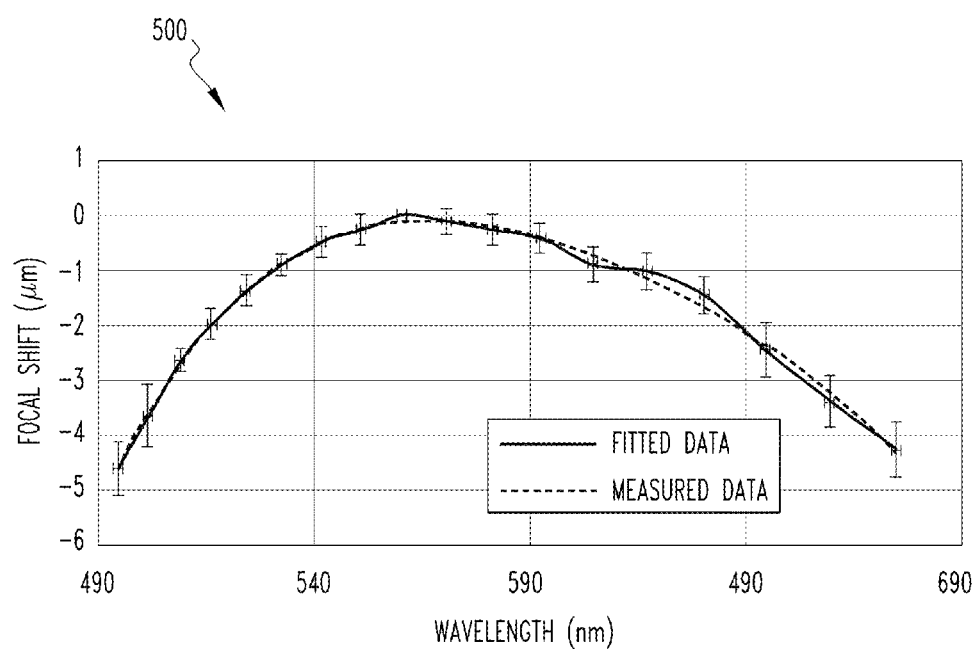
FIG. 5 illustrates an example, non-limiting chart of the dependence of focal plane on the wavelength.

FIG. 5 illustrates an example, non-limiting chart 500 of the dependence of focal plane on the wavelength. Each point was the average value from 20 measurements, and average focal shift curve with the error bar indicated standard deviation. To minimize the effect of noise, this curve (e.g., data) was fit with a fourth order polynomial (shown in curve 502 "fitted data") to find the focal-plane position at each wavelength.

Figure 6:
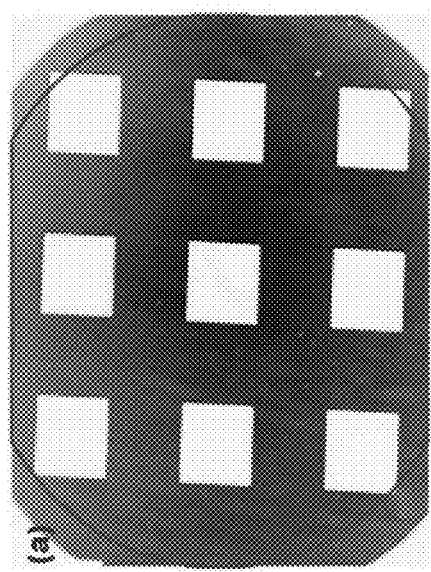
FIG. 6 illustrates an example, non-limiting correction for chromatic aberration-induced image distortion.
Figure 6:
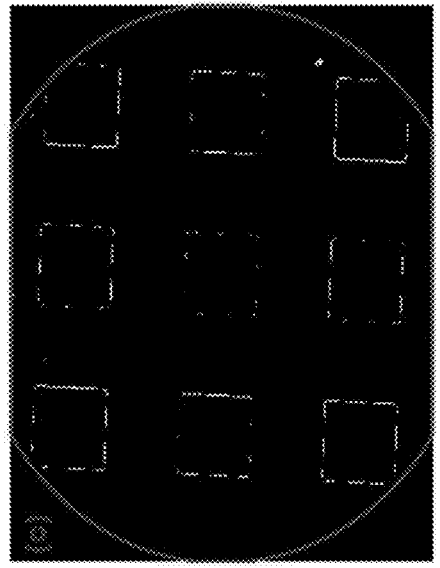
Figure 6:
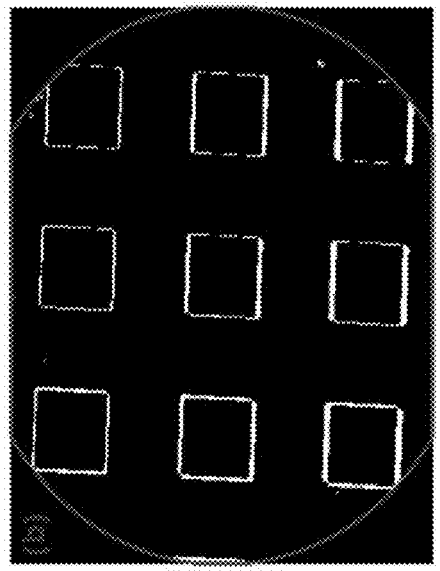

FIG. 6 illustrates an example, non-limiting correction for chromatic aberration-induced image distortion (shift). Due to chromatic aberration, there is a wavelength-dependent image distortion. To correct for such effect, a region-of-interest on the imaging standard, illustrated at 600, (e.g., using an image analysis micrometer, Edmund Optics) was imaged over the spectral range of interest (e.g., 490 to 680 nm) to obtain point estimates of location-dependent spectral drift at different locations, corresponding to the centroids of a nine-square grid covering the entire field-of-view. In one example, nine different locations were used for the point estimates. The point estimates were used to estimate the distortion field over the field-of-view for the spectral range using spline-based interpolation.

The distortion field for a specific wavelength is the estimate of the location-dependent translation that the image undergoes with respect to the image at the first wavelength. At 602 (before distortion correction), this distortion is illustrated as a difference image between the two wavelengths. Distortion correction reverses this translation to be within 2-5 pixels or ~500 nm, which is below the image resolution, as shown in the difference image at 604 (after distortion correction). By extending this correction to the entire spectral range, the undistorted spectral data cube is obtained, which is applied to each measured spectral cube I(x,y,k) before the phase map calculation.

To reliably identify the cell nuclei on the low-contrast drOPD map of unstained tissue, the transmission phase images of unstained and stained tissue are co-registered (e.g., using the image registration module). This may be performed by computing the affine transformation between the transmission phase images based on their similar image features and contrast. This is then applied to bright-field image of stained tissue to register the stained tissue with drOPD image of unstained tissue.

Image Registration of Unstained and Stained Tissue

Co-registration between unstained and stained tissue images is necessary in identifying nuclei locations in the unstained tissue image from segmented nuclei locations in the stained tissue image. A robust image registration requires similar image features present in the two images to be registered. However, the dramatically different image features in the low-contrast drOPD image of unstained tissue and the stain-absorption-based contrast of bright-field image of H&E-stained tissue present a challenge.

Figure 7:
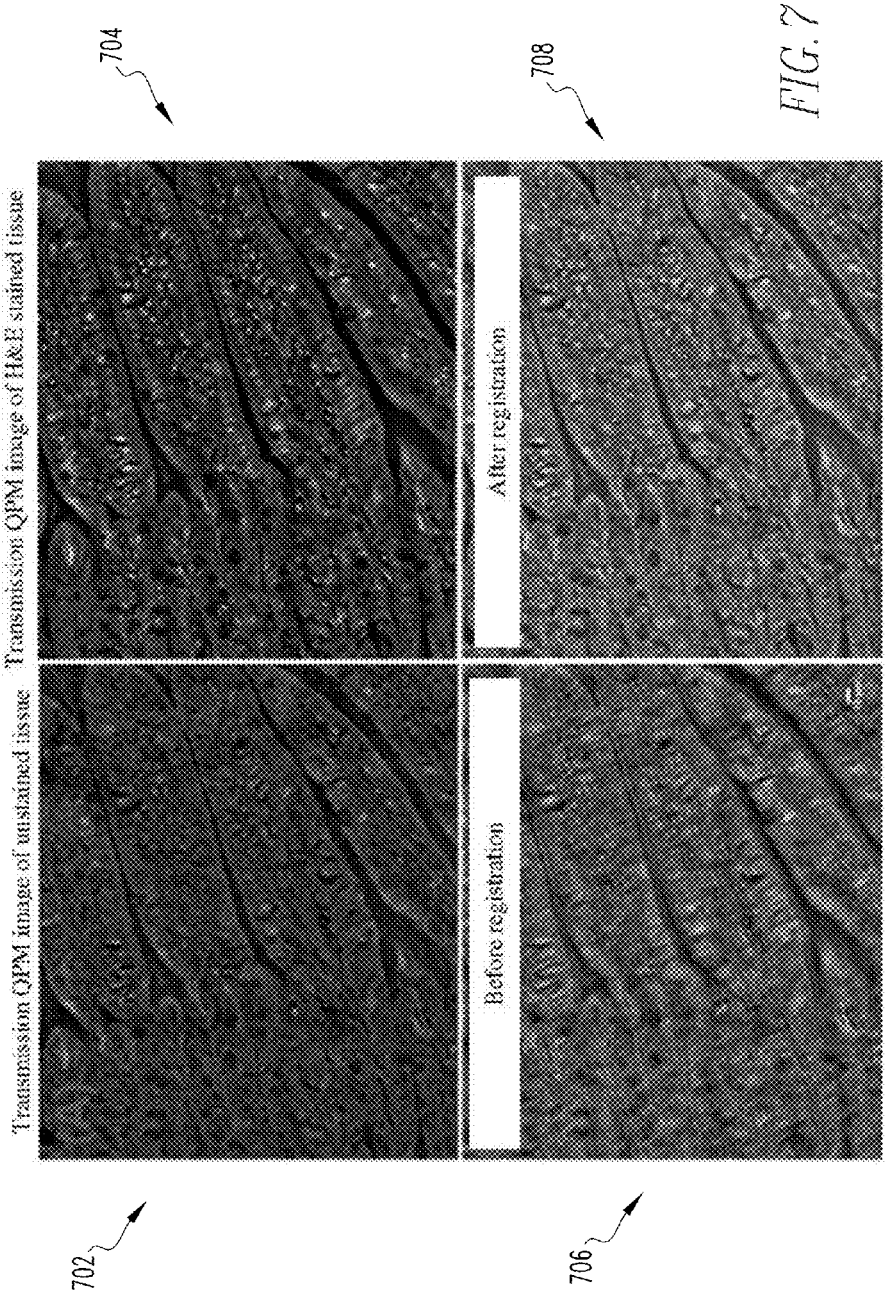
FIG. 7 illustrates image registration based on the transmission phase images of unstained and stained tissue.

FIG. 7 illustrates image registration based on the transmission phase images of unstained and stained tissue. Illustrated at 702 is the transmission QPM image of unstained tissue. Illustrated at 704 is the transmission QPM image of H&E stained tissue. It was observed that phase contrast generated by transmission phase is less affected by staining, as illustrated at 702 and 704, where transmission phase images of unstained and stained tissue have similar contrast profiles. This is exploited similarity in phase contrast to perform image registration. Specifically, using Otsu's method, both images are individually threshold to identify the foreground landmark features in each, which are nearly identical in unstained and stained phase images. Normalized cross-correlation between the segmented landmark features in the unstained and stained images are then used to estimate the translation, and log-polar fast Fourier transform is used to estimate the scaling and rotation.

With the microscope slide holder, it was observed that translation correction was sufficient for robust registration, because focus-correction eschewed the need to correct for scaling, and the slide holder successfully minimized rotations. As illustrated at 706 and 708, the overlaid transmission phase images of unstained and stained tissue before image registration (at 706) and after image registration (at 708), confirm the proper co-registration of the two images.

The registration was performed under the assumption that the mounted tissue sample did not move relative to the slide during tissue staining process. To ensure the validity of this assumption, tissue processing protocol was optimized with two strategies: (1) The glass slide is coated with poly-L-lysine to ensure good adherence of the tissue onto the slide; (2) The stepwise hydration-dehydration using graded alcohol (a step to remove paraffin) is used in both unstained and stained tissue processing to ensure minimal shrinkage. This protocol has been extensively tested to work in about 99% of the cases, with no tissue position shift after staining.

Nuclei segmentation may be performed on the registered bright-field image of the stained tissue to generate a nuclei mask that is applied to the drOPD image of unstained tissue at each depth for depth-resolved nanoNAM.

Cell Nuclei Segmentation

A segmentation GUI was developed to provide the operator with the ability to perform both manual and semi-automatic segmentation. The latter was based on constrained region-growing where the seed location within the nucleus was identified by the operator. The constraint was a relaxed convexity constraint to prevent unstable region growing and therefore ensuring a well-defined nuclear boundary. The segmentation GUI was also used to streamline the association between the segmented nuclei and their pathological class. Only the epithelial cell nuclei were segmented and confirmed by a pathologist. If the boundary of the single nucleus cannot be clearly determined either by direct visualization or semi-automatic segmentation method, that nucleus is not selected for analysis.

Figure 8:
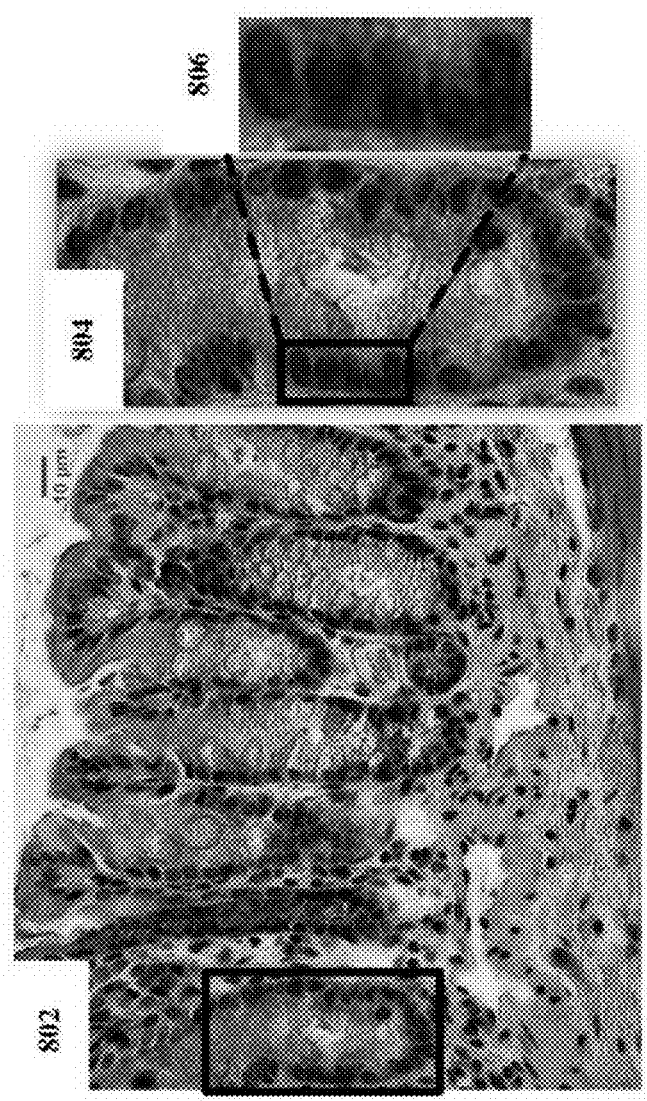
FIG. 8 illustrates an example, non-limiting bright-field image of hematoxylin and eosin-stained tissue, according to an aspect.
Figure 9:
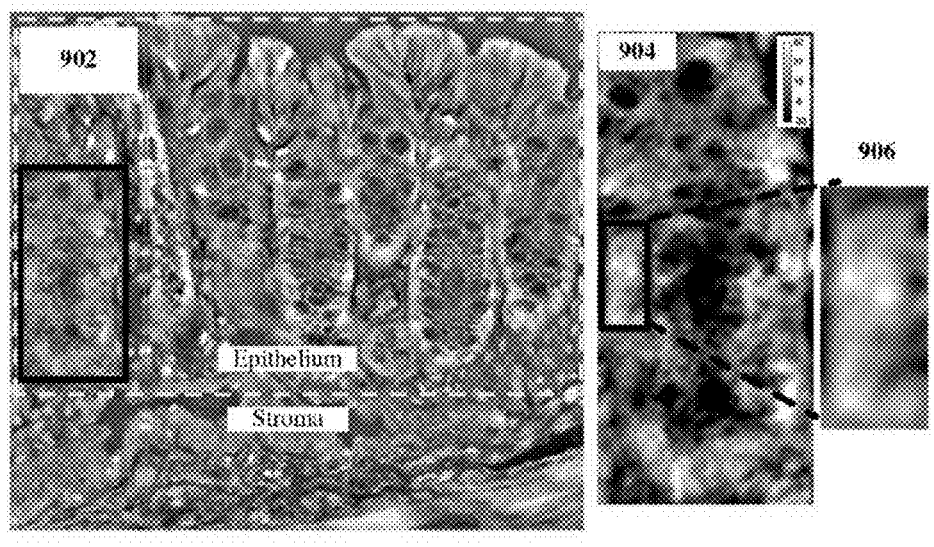
FIG. 9 illustrates an example, non-limiting transmission phase image of unstained tissue, according to an aspect.
Figure 10:
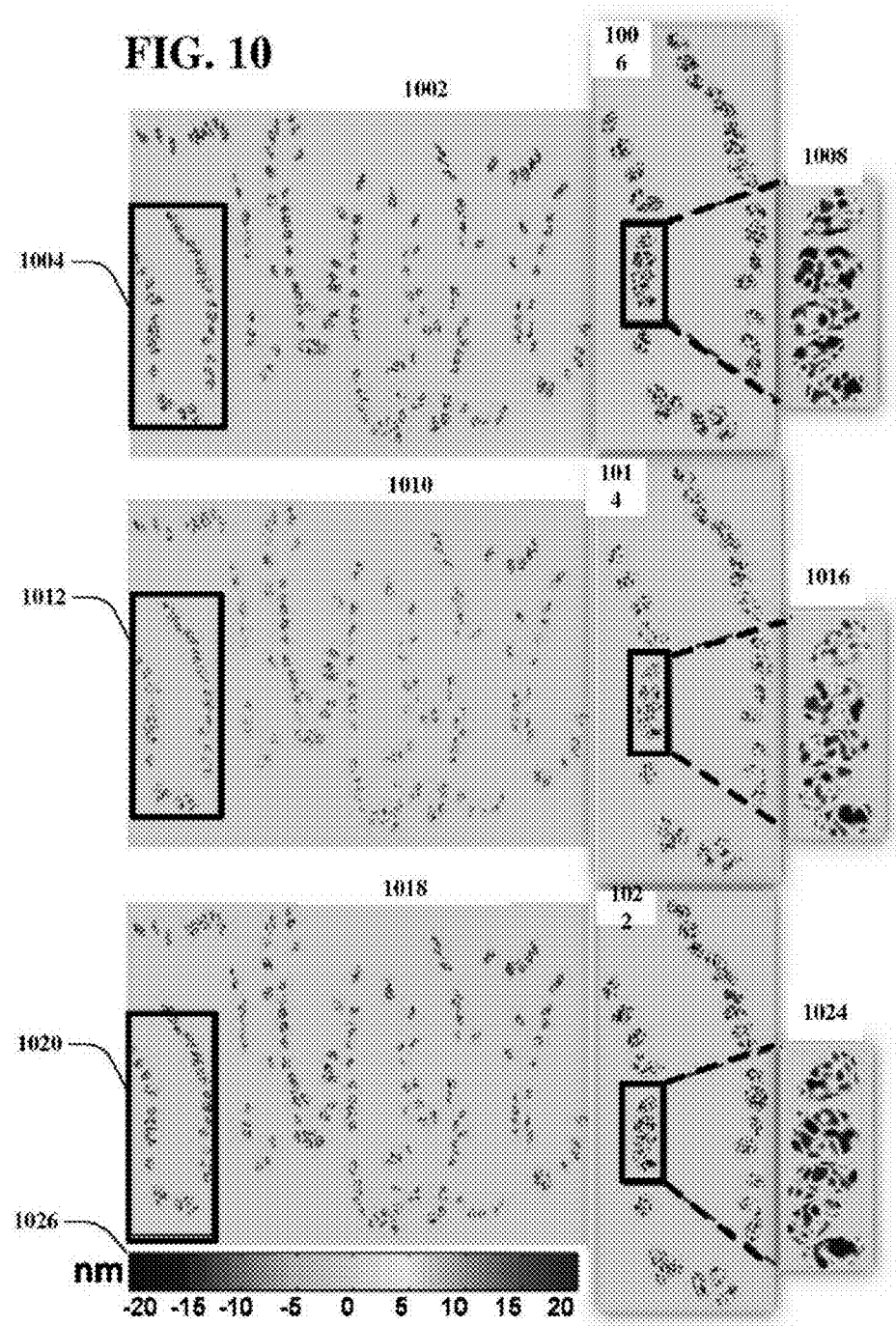
FIG. 10 illustrates example, non-limiting depth-resolved nanoscale nuclear architecture maps of unstained tissue, according to an aspect.

FIGS. 8-10 illustrate the output of nanoNAM and complementary characteristics of the three imaging modalities, according to various aspects. These figures illustrate nuclear architecture maps obtained from the three imaging modalities of the optical microscopy system 200.

FIG. 8 illustrates an example, non-limiting bright-field image 802 of H&E-stained tissue, according to an aspect. As a standard image for pathology evaluation, the bright-field image of H&E-stained tissue provides a clear identification of cell nuclei, as illustrated at 804. However, the image contrast of nuclear architecture is generated by the absorption of nuclear stains integrated along the entire tissue thickness, without sufficient details of internal architecture, as illustrated at 806.

FIG. 9 illustrates an example, non-limiting transmission phase image 902 of unstained tissue, according to an aspect. A transmission phase image provides high-contrast overall tissue architecture visualization for unstained tissue such as epithelium and stroma, for example. However, the nuclear architecture map comes from the integrated optical path length (OPL) through the entire tissue thickness and the individual epithelial cell nuclei cannot be unambiguously identified, as illustrated at 904 and 906.

FIG. 10 illustrates example, non-limiting depth-resolved nanoscale nuclear architecture maps of unstained tissue, according to an aspect. The illustrated architecture maps are derived from nanoNAM of segmented epithelial cell nuclei and reveal distinct patterns at three different depths, which are not visible in FIG. 8 and FIG. 9, discussed above.

Illustrated at 1002, is a central localization $Z_{OPL}$ at an optical depth of 1.35 μm. A first higher zoom inside the box 1004 is illustrated at 1006; a second higher zoom is illustrated at 1008. Illustrated at 1010 is an optical depth of 2.25 μm. A first higher zoom inside the box 1012 is illustrated at 1014; a second higher zoom is illustrated at 1016. Further, illustrated at 1018 is an optical depth of 3.15 μm. A first higher zoom inside the box 1020 is illustrated at 1022; a second higher zoom is illustrated at 1024.

Nuclear architecture is quantitatively described by the nano-scale drOPD value, as shown in the color bar 1026. The deeper red color (e.g., near number "20") represents higher drOPD, indicating higher change of refractive index or denser alteration in nuclear architecture. The reproducibility of drOPD value at a single-nucleus level over one-week repeated measurement with different acquisition time is 1 to 2 nm.

Reproducibility of drOPD

An extensive test was conducted to characterize the sensitivity and reproducibility of the optical system. First, drOPD stability was identified as key characteristic that determines the smallest detectable structural changes, that is, the structural sensitivity of drOPD. The temporal drOPD stability is characterized by taking the continuous measurement on an unstained tissue section slide for approximately 3 hours. The structural sensitivity (drOPD value) is quantified by the average of pairwise difference of different phase maps and the drOPD sensitivity over 60 by 60 pixel area (approximate size of a single nucleus) is 0.9 nm.

Second, the same unstained tissue section was measured once a day at three different acquisition time (20 ms, 50 ms, and 100 ms) over a one-week period, and quantified the reproducibility of the measured nanoscale nuclear architecture for the same segmented nuclei. Different acquisition times are used to mimic the possible intensity variation.

Figure 11:
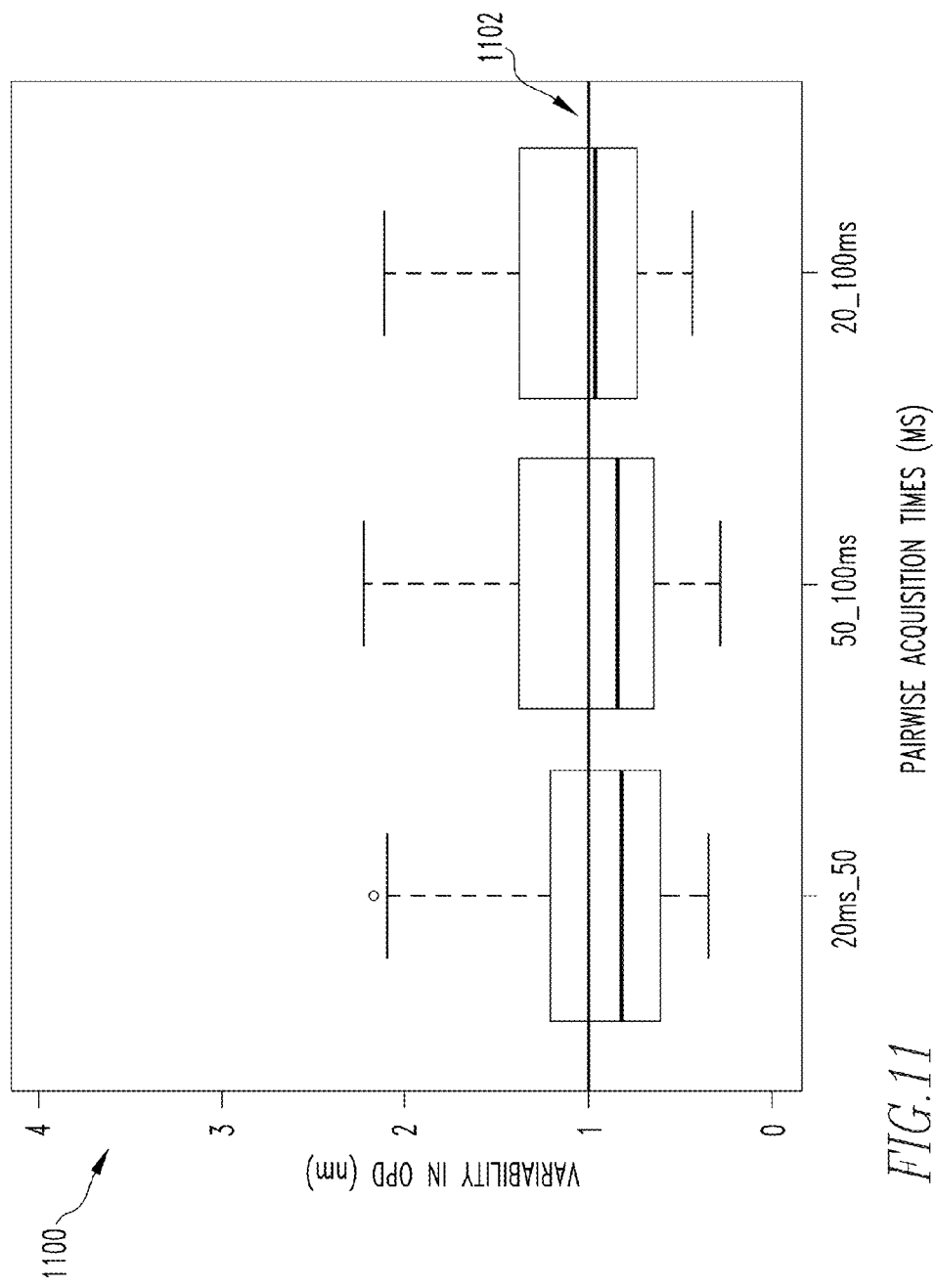
FIG. 11 illustrates a representation of reproducibility of mean-depth resolved optical path-length difference value at a single-nucleus level.

FIG. 11 illustrates a representation 1100 of reproducibility of mean-drOPD value at a single-nucleus level for approximately 150 cell nuclei. For each column, the box plot shows the variation of drOPD value for the pairwise difference of the same sample with different acquisition times (20 ms, 50, and 100 ms). The line 1102 indicates 1 nm. The average variation of the single-nucleus mean-drOPD is below 1 nm (line 1102), as shown in the dark line on each box plot.

As illustrated in FIG. 11, the box plot shows the variation of the mean-drOPD of each single-nucleus for the same set of nuclei on the tissue section over a one-week period. The pairwise difference between different acquisition time and different days is centered around 1 nm (indicated by the line 1102) with an upper bound of approximately 2 nm.

Calculation of drOPD Map

The spectral interference signal P(k) (information related to this will be provided in further detail below) from the sample area ($I_{sample}(x,y,k)$) and the reference signal $R_r$ on a background area (no sample) ($I_{ref}(x,y,k)$). After accounting for spectral response of the system, an inverse Fourier transform may be performed to obtain drOPD map at a set of predefined depth locations based on the following equation.

$$\delta p(x, y, z_{opl})_{sample} = \frac{\lambda_0}{2\pi} \arctan(\operatorname{Im}(F^{-1}(I_{final}))/\operatorname{Re}(F^{-1}(I_{final}))),$$ Equation 1 where $$I_{final} = \frac{I_{sample}(x, y, k) - 1_{ref}(x, y, k)}{1_{ref}(x, y, k)}.$$

Figure 12:
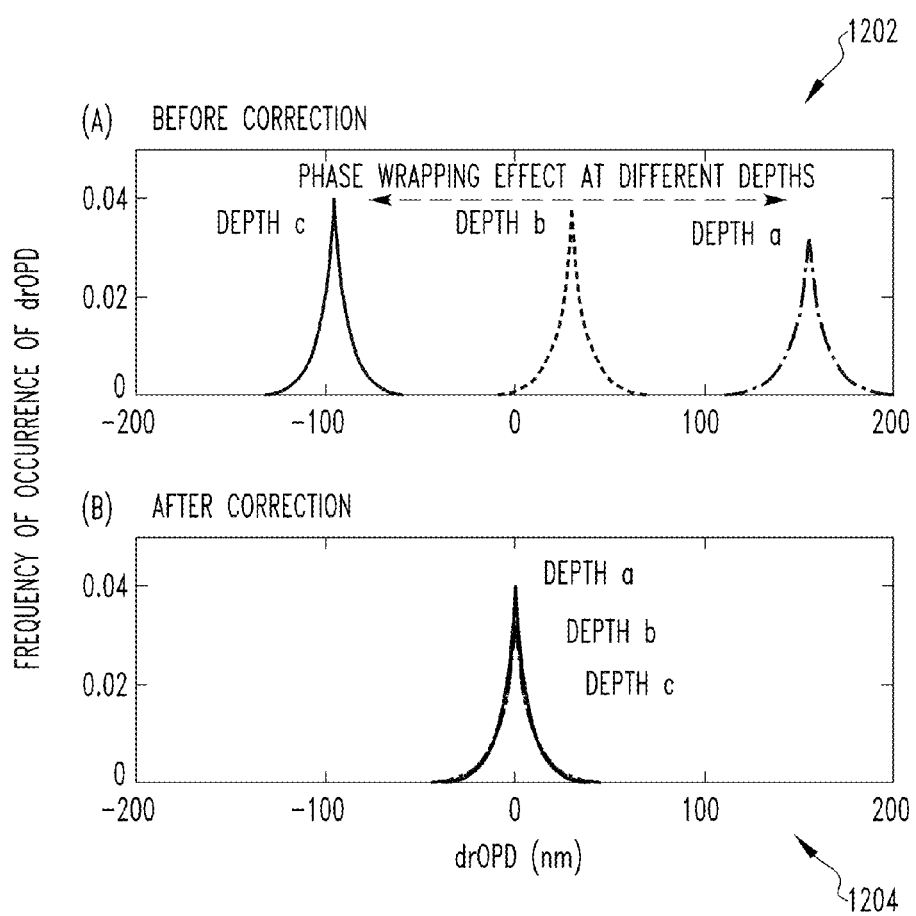
FIG. 12 illustrate a correction for baseline shift, according to an aspect.

As the tissue thickness may vary about ±0.5 μm for an FFPE tissue section, according to an example, a depth range of 1.35 to 3.15 μm for nanoNAM to be independent of thickness variation. The step size of 0.045 μm, although much smaller than the width of the coherence gate, may be used to capture the gradual change of the refractive index profile along the axial direction. Further to this example, background baseline correction was performed by calculating the phase map on a second background area without any sample present to obtain $\delta_p(x,y,z_{opl})_{bg}$ by replacing $I_{sample}(x,y,\lambda)$ in Equation 1 with $I_{bg}(x,y,\lambda)$ so that the drOPD map is calculated at each depth: $\delta p(x,y,z_{opl}) = \delta p(x,y,z_{opl})_{sample} - \delta p(x,y,z_{opl})_{bg}$, (as illustrated in FIG. 12). Further to this example, 2D (x-y plane) phase unwrapping may be performed based on an algorithm, such as a Goldstein algorithm, at each optical depth.

FIG. 12 illustrate a correction for baseline shift, according to an aspect. Before correction is illustrated at 1202 and after correction is illustrated at 1204. At 1202 is the drOPD distribution from the sample along the axial direction. The drOPD distribution from an image at three distinct optical depths shows a baseline shift as a result of the ramping effect of wrapped phase. After baseline correction, at 1204, the drOPD distribution at these three depths centers around 0.

Colitis Patient Identification

To aid in the understanding of aspects to the subject innovation, experimental results associated with specific experiments that were conducted are discussed herein. However, although for the purposes of obtaining the results discussed herein, specific choices were made as to the selection of various aspects of the experiments and associated setups—such as the disease being studied (e.g., cancer, as opposed to non-cancerous conditions; specific types of cancer, and so on), choice of specific statistical parameters, setup of optical apparatus, and so on—the various aspects discussed herein can be employed in other contexts as well.

In connection with the experiments discussed herein involving human specimens were performed and all specimens were collected with the approval of the Institutional Review Board at University of Pittsburgh. The experiments were conducted by retrospectively reviewing pathology reports for a defined period of time in TIES (a web-based application to search through pathology reports of all UPMC affiliated hospitals) for colitis patients who underwent standard surveillance colonoscopy. High-risk patients are defined as those who subsequently developed HGD or colorectal adenocarcinoma during the follow-up after more than 1 year of the initial surveillance colonoscopy, and low-risk patients are defined as those who did not developed any HGD or adenocarcinoma in the follow-up. Their FFPE tissue blocks of the colon tissue biopsies were retrieved from the initial surveillance colonoscopy in which the pathologic status had no HGD oradenocarcinoma. The slides were reviewed by an expert gastrointestinal pathologist to confirm those cell nuclei for nanoNAM to be histologically normal and grade the inflammation. The person who performed data acquisition and nuclei segmentation was blinded to clinical diagnosis.

Statistical Analysis

In one experiment, the nuclear architecture characteristics was quantified using two statistical parameters: mean-drOPD and entropy. The mean-drOPD of each nucleus was calculated by taking the average value of all the positive drOPD values in the nuclear architecture map of each nucleus, as the positive drOPD represents increasing change of refractive index nuclear architecture. Entropy is calculated for each nucleus using the relation:

$$E_{OPL} = -\sum_{i=0}^{N-1} p(\delta p_i) \log_2(\delta p_i),$$

where drOPD is considered to be a discrete random variable $\delta p_i$, ranging from $\delta p_o$ to $\delta p_{N-1}$, and with probability mass given by $p(\delta p_i)$.—To obtain the scatter plot, take the average value of mean-drOPD and entropy over approximately 300 to 500 cell nuclei from a specific pathology type [normal, low-grade dysplasia (LGD), or HGD] for each subject. The LIFETEST procedure (SAS statistical software) was used to compute Kaplan-Meier estimates of the survivor functions and compare survival curves between groups of patients using the log-rank test. The cutoff point for mean-drOPD and entropy was mathematically determined using an established method.

Calculation of Quantitative Microscale Image Features of Nuclear Architecture

For a side-by-side comparison between nanoNAM, gold standard of conventional pathology, and digital image analysis, standard bright-field images (NA=0.4, magnification=45) of H&E-stained tissue of colon biopsies obtained at the initial surveillance colonoscopy of colitis patients were used and twelve nuclear features belonging to three broad categories were extracted. These broad categories are morpho-logic, statistical, and textural—typically considered in conventional image analysis—based histopathologic quantification, using the same set of cell nuclei for nanoNAM. The morphologic features describe the area, perimeter, roundness, and elongation of the nuclei. The statistical features characterize the mean, SD, skewness, and kurtosis of nuclear intensity distribution. In addition to looking at the moments of the intensity distribution, Haralick features were used to describe the spatial arrangement of nuclear intensity, thereby characterizing nuclear texture. Specifically four Haralick features were examined, which are nuclear contrast, pixel correlation, uniformity, and homogeneity. The average value for the same set of nuclei used for nanoNAM was used for each patient in the scatter plot. Statistical comparison between low risk and high risk was performed using the two-sided Student t test at 95% confidence interval.

Results nanoNAM During Cancer Development Using an Animal Model of Colon Carcinogenesis First, a nanoNAM was performed to analyze epithelial cell nuclei during cancer progression using a well-established animal model of colorectal carcinogenesis. This animal model of colorectal carcinogenesis is a chemical-induced colitis-associated colorectal cancer developed in the background of chronic inflammation, in which mice treated with the inflammatory agent dextran sulfate sodium (DSS) and a carcinogen azoxymethane.

Animal Models

All animal studies were performed in accordance with the institutional Animal Care and Use Committee of the University of Pittsburgh. All mice were housed in micro isolator cages in a room illuminated from 7:00 AM to 7:00 PM (12:12-hr light-dark cycle), with access to water and chow ad libitum.

Colitis-Associated Mouse Model of Colorectal Carcinogenesis

To induce colitis as a control for chronic inflammation, three C57BL/6J mice (JAX stock#000664) at 5-6 weeks were treated with three 7-day cycles of the inflammatory agent dextran sulfate sodium (DSS) at 2.5% in the drinking water. To induce colitis-associated colorectal cancer (CRC), three C57BL/6J mice were first injected with 12.5 mg/kg azoxymethane (AOM), then treated with three 7-day cycles of 2.5% DSS. After 2 months of recovery, the mice were sacrificed and the colon tissue was harvested and prepared in bundles of 0.5 cm segments. As confirmed by the expert pathologist, three DSS-treated mice developed chronic inflammation without any dysplasia; two DSS/AOM-treated mice developed low-grade dysplasia (LGD), and one mouse developed high-grade dysplasia (HGD).

Figure 13:
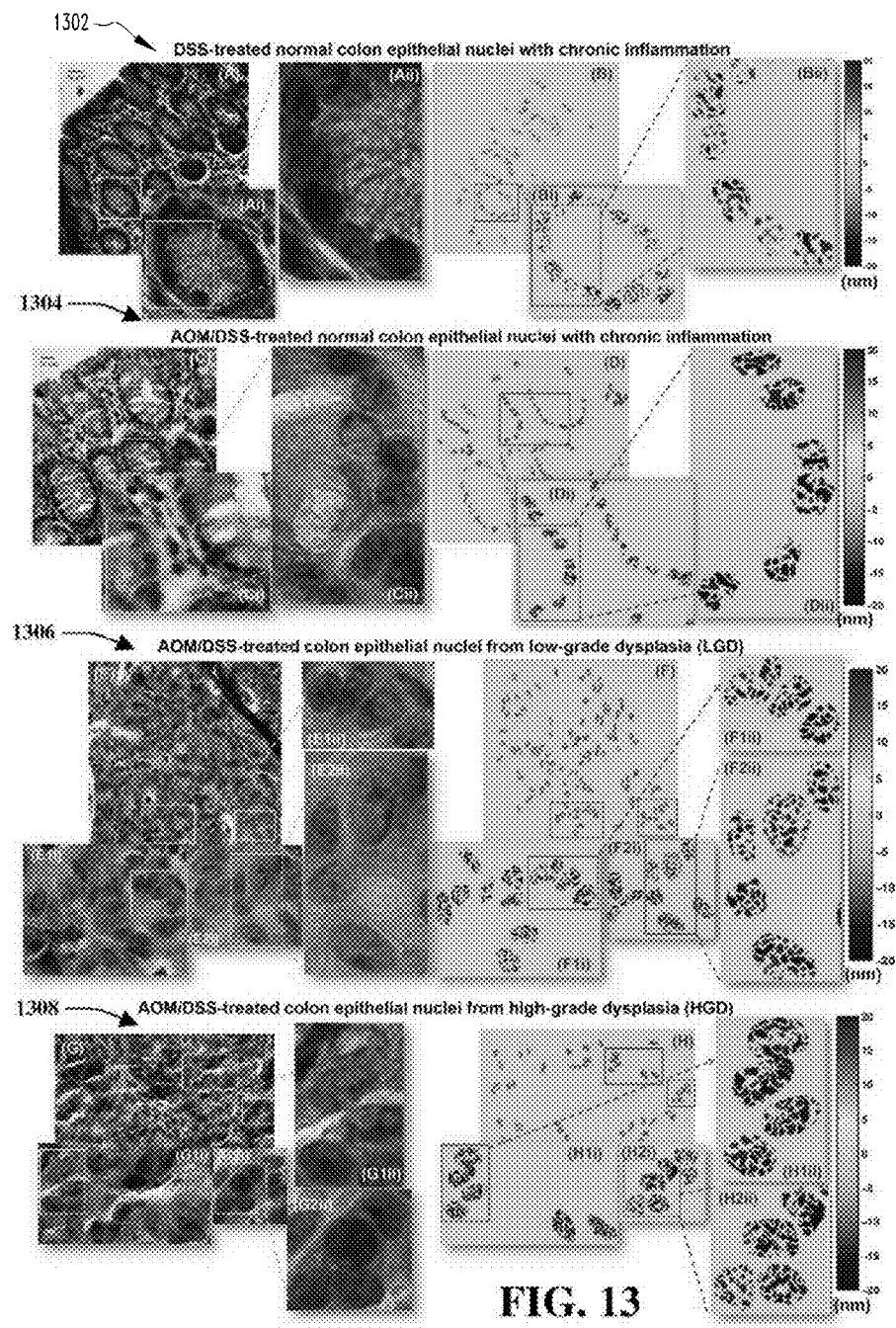
FIG. 13 illustrate the nanoscale nuclear architecture mapping on colonic epithelial cells from unstained tissue at different stages of cancer development in an animal model of colitis-associated colon carcinogenesis in which dysplasia is developed in the background of chronic inflammation.

FIG. 13 illustrate the nanoNAM on colonic epithelial cells from unstained tissue at different stages of cancer development in an animal model of colitis-associated colon carcinogenesis in which dysplasia is developed in the background of chronic inflammation.

In FIG. 13, the left plot illustrates the bright-field images of H&E stained colon tissue, and the right plot illustrates the corresponding nanoscale nuclear architecture maps of unstained tissue in which the depth-resolved map is averaged along the optical-depth ranges of 1.3 µm to 3.2 µm. The images are from normal cells in control mice (DSS-treated mice, chronic inflammation only; A and B at 1302), histologically normal-appearing cells in an AOM/DSS-treated mouse (C and D at 1304), histologically low-grade dysplasia (E and F at 1306), and high-grade dysplasia in AOM/DSS-treated mice (G and H at 1308). Elements Ai-H2i and Aii-H2ii are the progressively higher zooms of the regions inside the solid boxes and the dashed boxes. The color bars (at the right of the figure) illustrate the drOPD value in nanometers.

The nanoNAM was performed on four groups of cell nuclei correlating with cancer progression: (A-B) histologically normal colonic epithelial cell nuclei in DSS-treated mice that developed chronic inflammation without dysplasia as illustrated at 1302, (C-D) histologically normal epithelial cell nuclei in AOM/DSS-treated mice that developed dysplasia as illustrated at 1304, (E-F) dysplastic cell nuclei from LGD as illustrated at 1306, and (G-H) HGD as illustrated at 1308, all confirmed by an expert pathologist. The depth-resolved nuclear architecture maps were summarized through an "average" map in which the depth-resolved maps along the optical-depth range of 1.3 to 3.2 µm were averaged, as illustrated in FIG. 13.

The average nuclear architecture maps exhibit progressively higher drOPD, or denser architectural alteration (e.g., increasing change of refractive index), as indicated by more prevalent areas of deeper red color, correlating with cancer progression. Such change is detectable even at an early stage of cancer development when the epithelial cells still appear histologically normal (illustrated at 1304, C and D) than those from mice with just chronic inflammation (illustrated at 1302, A and B). The denser change in nuclear architecture (deeper red color) becomes more prominent and spatially extended in histologically dysplastic cells identified by the expert pathologist, consistent with the well-known nuclear architecture characteristics in cancer cells—coarse aggregation of condensed chromatin—commonly used for cancer diagnosis. The HGD nuclei show a higher drOPD value than those from LGD.

Figure 14:
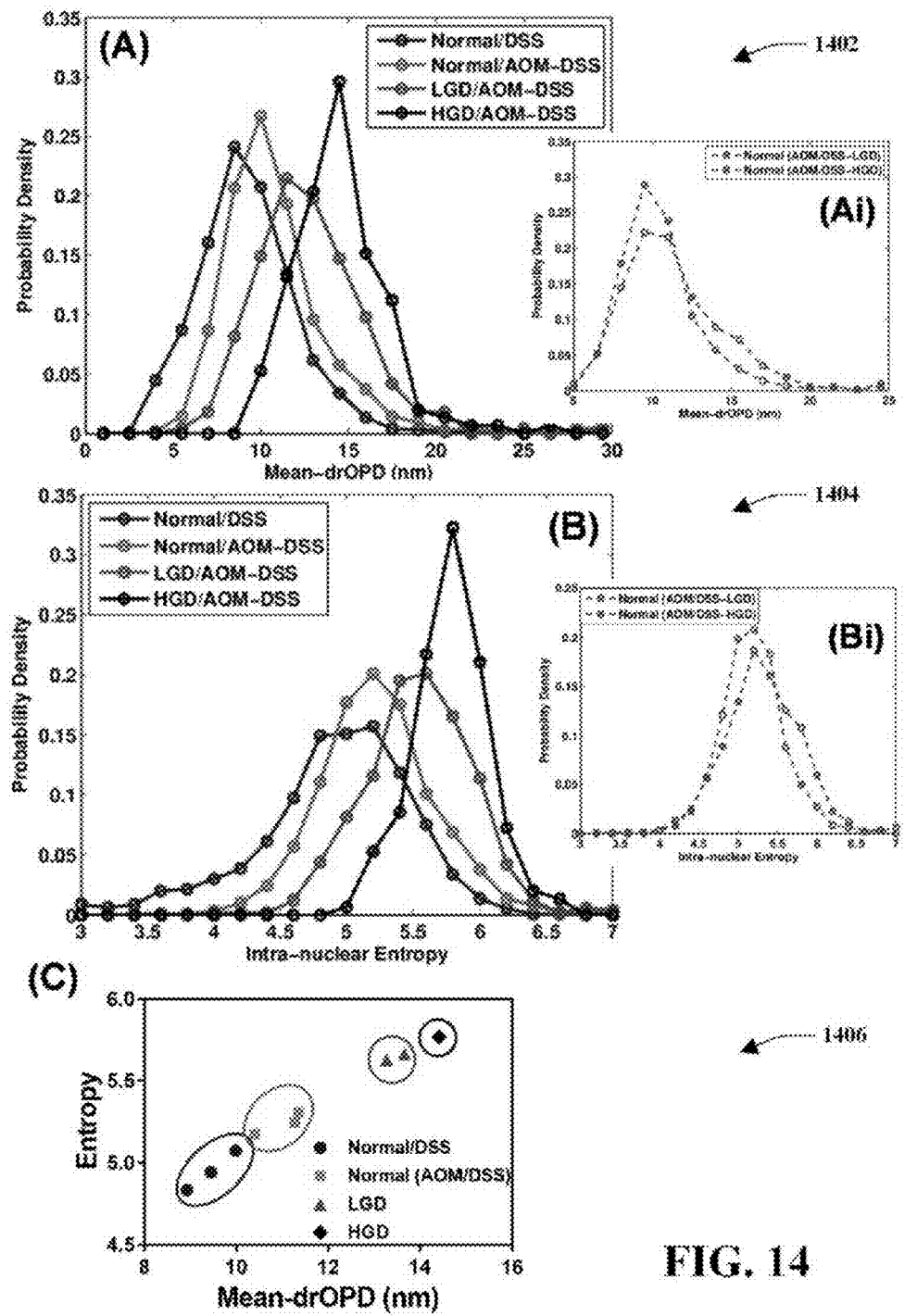
FIG. 14 illustrates quantitative analysis of nanoscale nuclear architecture mapping on dextran sulfate sodium and dextran sulfate sodium/azoxymethane-treated mice.

FIG. 14 illustrates quantitative analysis of nanoNAM on DSS and DSS/AOM-treated mice. At 1402 is a histogram of mean-drOPD and, at 1404, is intranuclear entropy derived from nanoNAM performed on histologically normal cells from DSS-treated (dash-dot-circle), DSS/AOM-treated (dash diamond) mice, and the dysplastic cells from LGD (dot square and HGD (solid plus). The figure inserts (Ai and Bi) illustrate the histogram of mean-drOPD (Ai) and intranuclear entropy (Bi) in histologically normal cells from the mice that developed HGD (solid plus) compared with those that developed LGD (dashed circle). Only positive values of drOPD in the nuclear architecture maps were used to characterize denser nuclear architecture alteration.

At 1406 is a scatter plot of averaged mean-drOPD versus entropy for each mouse treated with DSS (circle) and AOM/DSS (square, triangle, and diamond). Each point was calculated by averaging nuclear architecture features for al nuclei with a specific pathology type (normal, LGD, or HGD) from each mouse.

The image features of nuclear architecture maps are further quantified by two parameters for each nucleus—mean positive drOPD within each nucleus, referred to as mean-drOPD, characterizing the degree of denser change of nuclear architecture, and intranuclear entropy characterizing the nuclear architecture disorder. The histogram of mean-drOPD and entropy for the four groups of cell nuclei discussed above with respect to FIG. 13 are illustrated at 1402 and 1404, respectively. The histogram of mean-drOPD has a wide spread, due to the intrinsic biologic heterogeneity.

Overall, however, the histogram of mean-drOPD and entropy show a progressively higher value correlating with cancer progression, from normal nuclei with chronic inflammation, to histologically normal-appearing nuclei from AOM/DSS-treated mice with dysplasia, to LGD nuclei, to the most pathologically advanced HGD nuclei. This result, based on the statistical analysis of several thousand nuclei, further confirms a progressively more dense and disorganized alteration in nuclear architecture during cancer progression, even at histologically normal stage prior to the detection of dysplasia. Interestingly, the histogram of histologically normal cells from mice that developed HGD shifts toward higher mean-drOPD and entropy, compared with those mice that only developed LGD (FIG. 14, Ai-Bi), suggesting the potential of nanoNAM on histologically normal cells to detect the clinically significant HGD. Furthermore, on an individual subject's level, the average value of single-nucleus mean-drOPD and entropy from all nuclei (~300-600 nuclei per subject) with a specific pathologic type (normal, LGD, HGD) for each subject is shown as a scatter plot 1406 in FIG. 14.

The nanoNAM-derived markers from dysplastic cells with pathologically detectable microscopic nuclear abnormality (LGD and HGD) are well separated from normal cells by a large difference. The nanoNAM of cells that appear histologically normal to the expert pathologist can also distinguish those mice with just chronic inflammation (diamond) from those mice that developed dysplasia (square), even though with a smaller difference than the distinction between normal (circle and square marker) and dysplastic cells (triangle and diamond marker). This result shows the promise of nanoNAM to detect early-stage cancer development. It was further confirmed that nanoNAM-derived progressively denser alteration of nuclear architecture is indeed characteristic of cancer progression, rather than the side effect of the drug treatment or animal specific, with another animal model of a spontaneous development of colorectal cancer—$Apc^{Min/+}$ mice that develop multiple intestinal neoplasms (Min) due to a germ-line mutation in adenomatous polyposis coli (Apc) gene.

$Apc^{Min/+}$ Mouse Model

A total of 12 female mice were included in this study and fed the AIN-93G diet to facilitate the development of polyps from 4 weeks of age until sacrifice. A first set of three C57BL/6J wild-type mice and three age- and sex-matched C57BL/6J and $Apc^{Min/+}$ (JAX stock number 002020) mice were sacrificed at 6 weeks of age. A second set of three $APC^{Min/+}$ mice and $Apc^{Min/+}$ mice were sacrificed at 12 weeks of age. The 6-week $Apc^{Min/+}$ mice did not show any visible tumor or dysplasia as confirmed by the pathologist; whereas those 12-week $Apc^{Min/+}$ mice had developed multiple visible adenomatous polyps and histologically visible dysplasia in their small intestine. The small intestines tissue was removed, washed with phosphate buffered saline, and prepared in bundles of 1 cm segments as described. The tissue was fixed in 10% neutral buffered formalin for over 24 hours, and the tissue was embedded in paraffin block. A segment of colon (both proximal and distal parts) was cut, and the tissue was placed in 10% neutral buffered saline for over 24 hours. Then the tissue was embedded in paraffin block.

To prepare an unstained slide, a 5-μm tissue section was obtained and placed on the coated slide with the same protocol as described herein. The nanoNAM was performed on three groups of cell nuclei: (1) histologically normal intestinal epithelial cell nuclei from 6-week wild-type and age-matched $Apc^{Min/+}$ mice, an early-stage of carcinogenesis without visible tumor; (2) histologically normal intestinal epithelial cell nuclei at 12 weeks; (3) histologically dysplastic cells at 12 weeks, a cancer stage with visible tumors in the small intestines.

The results of the experiment indicated that at 6 weeks, it is an early-stage cancer development, with no visible tumor or dysplastic tissue found in the small intestine; while at 12 weeks, visible tumors can be seen in the small intestinal tissue of $Apc^{Min}$ mice. In the histologically normal intestinal epithelial nuclei, there are progressively higher mean-drOPD and entropy values in 6-week and 12-week $Apc^{Min/+}$ mice compared to those normal cell nuclei from the age-matched wild-type mice. In histologically dysplastic cell nuclei, higher prevalence of higher mean-drOPD or deeper red in the nanoscale nuclear architecture maps can be seen compared to those of normal cells. This result confirmed the previous finding in AOM/DSS-treated mouse model, that nanoNAM-derived progressively denser alteration of nuclear architecture is indeed characteristic of cancer progression, rather than the side-effect of the drug treatment or animal specific.

nanoNAM to Predict "Future" Cancer Progression in Ulcerative Colitis Patients

As a proof-of-concept, it was demonstrate that the potential clinical use of nanoNAM to predict "future" cancer progression in a retrospective clinical study with ulcerative colitis patients who had up to 13 years of surveillance colonoscopy follow-up. Using Pathology Database at University of Pittsburgh Medical Center, fifteen high-risk patients (or progressors) who developed HGD or colorectal cancer after at least more than one year were identified.

These high-risk patients are matched with eighteen low-risk patients (or nonprogressors) who did not develop any HGD or colorectal cancer during the follow-up, in which none of the available clinical and pathologic factors has any bias between low-risk and high-risk group.

To ensure that the low-risk patients indeed did not develop cancer, we selected those patients with an average of 8.7 follow-up years, compared with an average of 4.3 follow-up years in high-risk patients. The archived FFPE tissue block of colon tissue biopsies obtained at the time of the initial surveillance colonoscopy was retrieved and nanoNAM was performed on the histologically normal epithelial nuclei on the unstained slide from the initial colon tissue biopsies. As most patients had no dysplasia with a small percentage of tubular adenoma, indefinite for dysplasia and LGD that represent the actual clinical scenario, nanoNAM focused on those histologically normal cells to ensure the consistency of pathology type, confirmed by an expert gastrointestinal pathologist.

Figure 15:
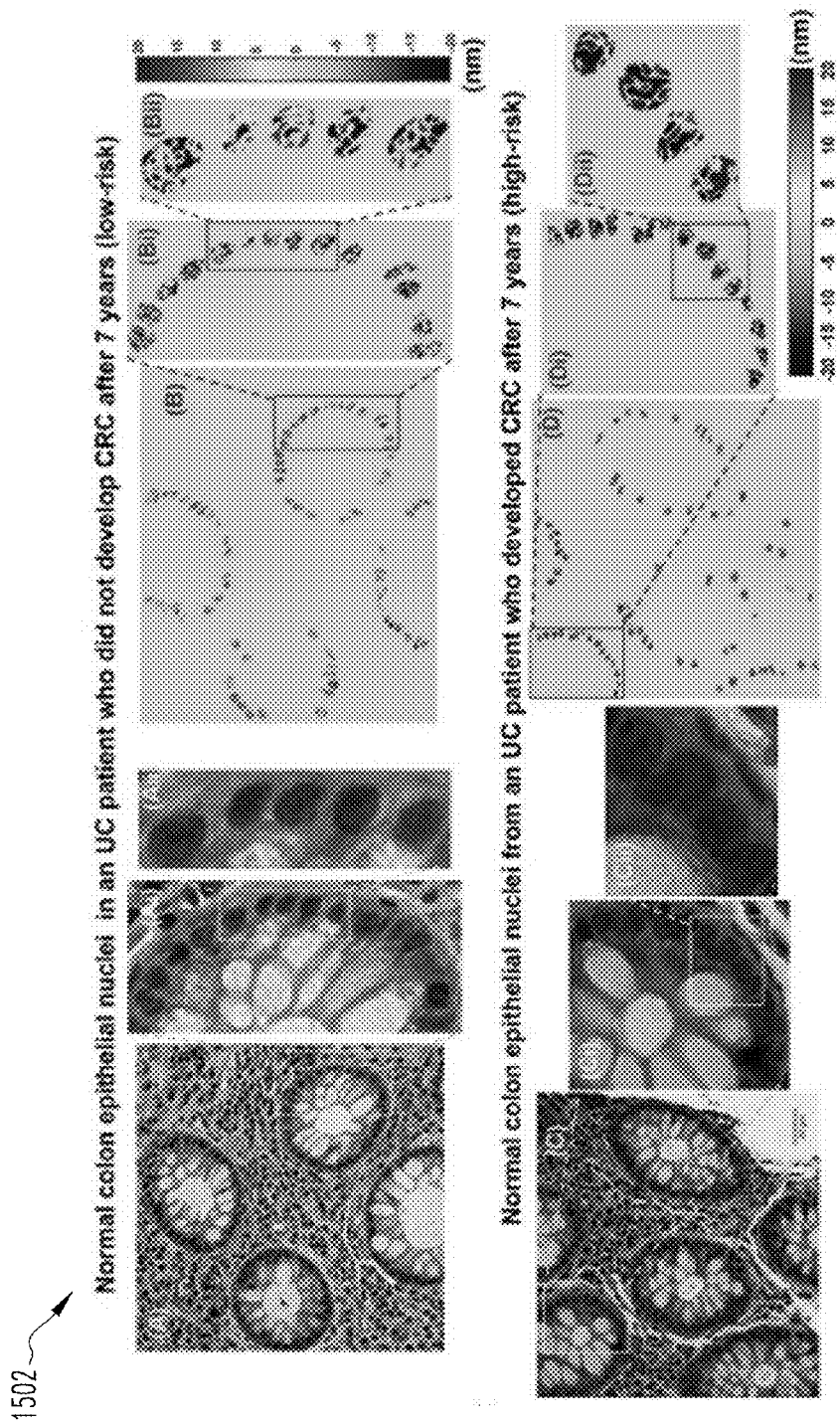
FIG. 15 illustrates the representative depth resolved optical path-length difference maps of the initial normal tissue biopsy from a low-risk ulcerative colitis patient and a high-risk ulcerative colitis patient.

FIG. 15 illustrates the representative drOPD maps of the initial normal tissue biopsy from a low-risk ulcerative colitis patient and a high-risk ulcerative colitis patient. The nanoNAM on normal colonic epithelial cells of unstained tissue from a ulcerative colitis (UC) patient who did not develop HGD or colorectal cancer (CRC) after 7 years of follow-up (low-risk) is illustrated at 1502. The nanoNAM on normal colonic epithelial cells of unstained tissue from a ulcerative colitis (UC) patient who developed colon adenocarcinoma after 7 years (high-risk) is illustrated at 1504.

The bright-filed images (A and C) and nanoscale nuclear architecture maps (B and D) of histologically normal colon tissue from low-risk (A and B) and high-risk (C and D) ulcerative colitis patient. Ai-Dii are the progressively higher zooms of the regions inside the yellow (e.g. light) and red (e.g., dark) boxes. The color bar illustrates drOPD value in nanometers.

FIG. 15 shows the representative drOPD maps averaged along the optical-depth range of 1.3 to 3.2 µm. Further, the low-risk ulcerative colitis patient did not develop HGD or colorectal cancer during 7 years of follow-up, and the high-risk ulcerative colitis patient developed colorectal cancer after 7 years. The cell nuclei from the high-risk patient (illustrated at 1502) show denser architecture alteration, compared with those from the low-risk patient (illustrated at 1504), consistent with our observation in the animal models of colorectal cancer progression.

Then the mean-drOPD and entropy of each nucleus was calculated for approximately 300 to 600 normal-appearing nuclei per patient and the histogram of single-nucleus mean-drOPD and entropy for each patient.

Figure 16:
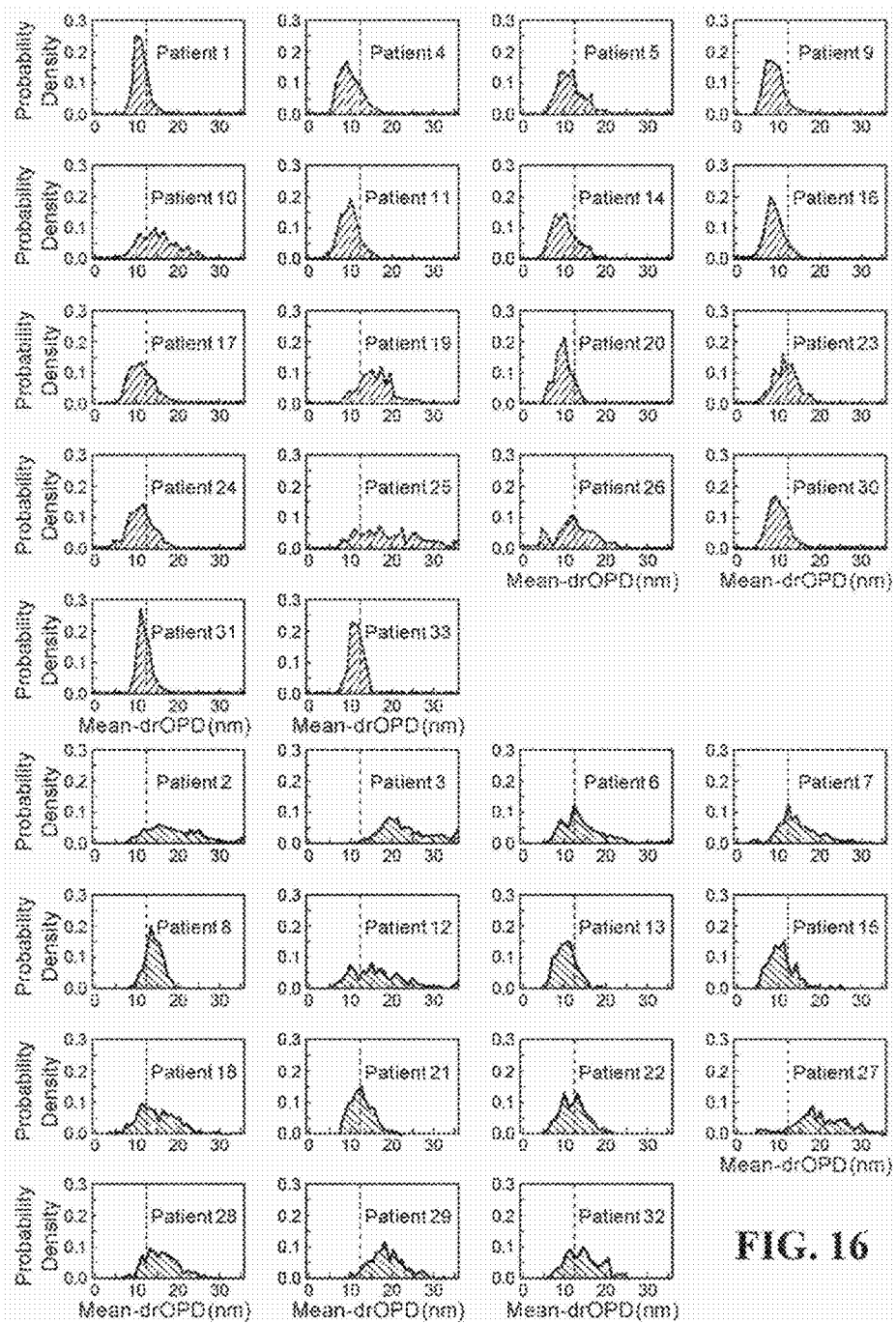
FIG. 16 illustrates the histogram of mean-depth resolved optical path-length difference for low-risk and high-risk patients.

FIG. 16 illustrates the histogram of mean-drOPD for low-risk (dashed line) and high-risk patients (solid lines). According to results of the experiments, the histogram from most high-risk patients (except patients 13 and 15) was created and shows a shift toward higher mean-drOPD with a broader distribution compared with that from most low-risk patients (except patients 10, 19, and 25). The dashed black line is the cutoff value for mean-drOPD (12.3 nm) that best distinguishes high-risk from low-risk patients.

As illustrated in FIG. 16, the histogram of high-risk patients shifts toward higher mean-drOPD with a broader distribution (solid lines), suggesting denser alteration of nuclear architecture and greater nuclear heterogeneity, compared with those from low-risk patients (dashed lines). The mean-drOPD and entropy values are then averaged over all nuclei for every patient to generate single-patient mean-drOPD and entropy, used as the patient characteristics.

Figure 17:
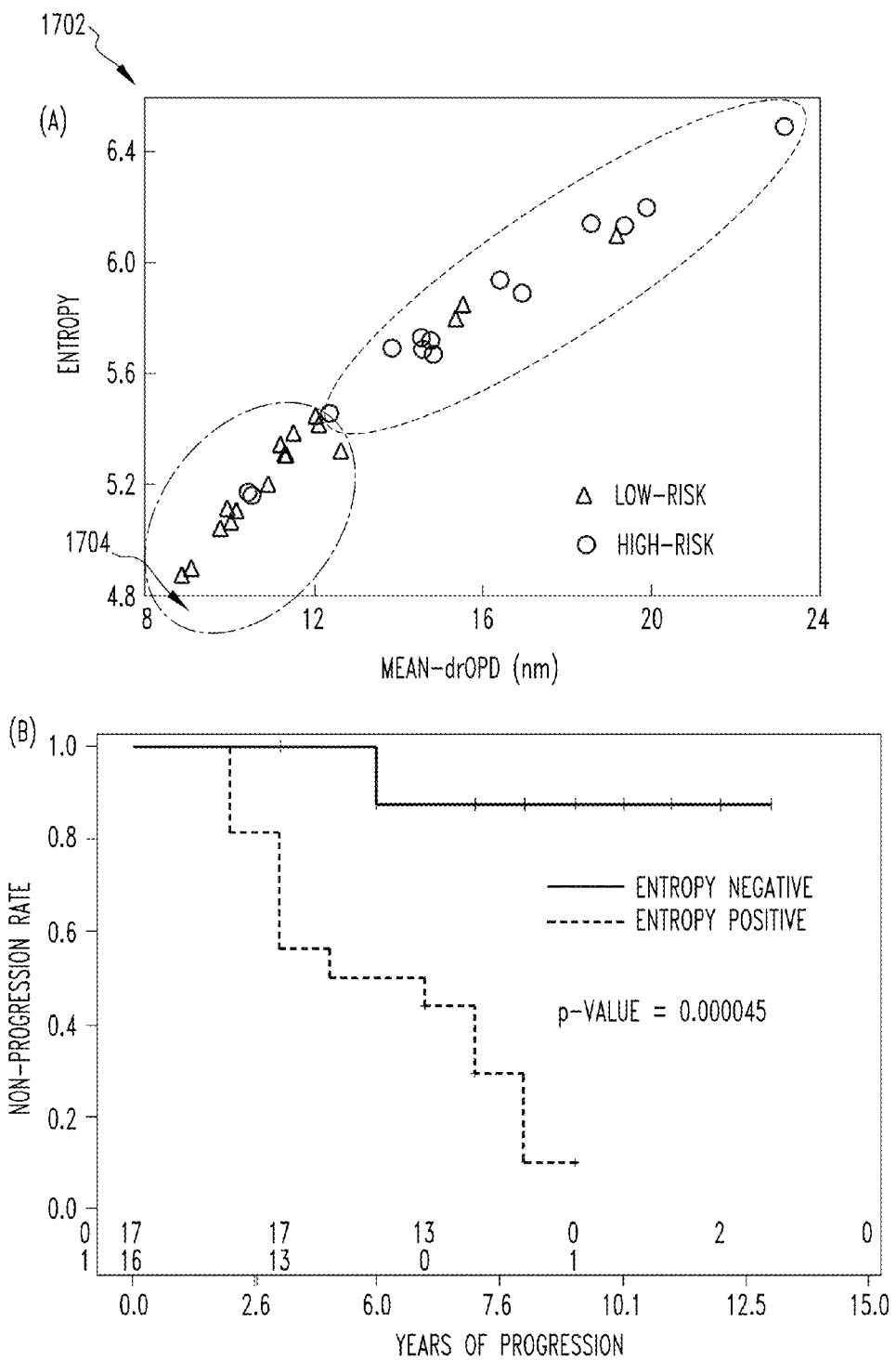
FIG. 17 illustrates statistical analysis of nanoscale nuclear architecture mapping-derived nuclear architecture features of histologically normal cells from the initial surveillance colonoscopy biopsies of colitis patients.

FIG. 17 illustrates statistical analysis of nanoNAM-derived nuclear architecture features of histologically normal cells from the initial surveillance colonoscopy biopsies of colitis patients. At 1702 is illustrated a scatter plot of mean-drOPD versus entropy for high-risk (circle) and low risk (triangle) colitis patients. At 1704 is illustrated a Kaplan-Meier curve using entropy as the estimator. The entropy positivity is defined as those above the cutoff value of 5.45.

As illustrated in the scatter plot (FIG. 17 at 1702), the nanoNAM-derived single-patient mean-drOPD and entropy separate high-risk from low-risk group and correctly classify 12 of 15 high-risk and 15 of 18 low-risk patients. At 1704 is illustrated the Kaplan-Meier curve for time-dependent cancer progression using entropy as the estimator. Intranuclear entropy shows a high level of statistical significance in predicting HGD/colorectal cancer progression over time (log-rank test, P value=0.0.000045). The similar statistical significance is observed using mean-drOPD as the estimator (P value=0.0033).

Further, the results were compared with both gold standard and widely used quantitative analysis of standard histology images. First, the expert pathologist went back and reviewed all the slides used for nanoNAM and did not identify any distinct pathologic features in high-risk patients. Next, it was evaluated whether quantitative microscale nuclear architecture from bright-field image of H&E-stained tissue can distinguish high-risk from low-risk patients.

Figure 18:
FIG. 18 illustrates scatter plots of quantitative image features of microscale nuclear architecture extracted from the microscopic bright-field images of hematoxylin and eosin-stained tissue of colon biopsies obtained at the initial surveillance colonoscopy for low-risk and high-risk colitis patients.

FIG. 18 illustrates scatter plots of 12 quantitative image features of microscale nuclear architecture extracted from the microscopic bright-field images of H&E-stained tissue of colon biopsies obtained at the initial surveillance colonoscopy for low-risk (solid dots) and high-risk (hollow circles) colitis patients. The 12 quantitative image features are nuclei area, perimeter, roundness, elongation, mean, SD, skewness, kurtosis, contrast, homogeneity, correlation, and uniformity. Each scatter plot shows two of the 12 image features.

Continuing the above experiment, on the same set of cell nuclei analyzed by nanoNAM, we calculated 12 commonly used microscale image features (e.g., 4 morphologic, 4 statistical, and 4 textural), which do not separate high-risk from low-risk patients (FIG. 18) as much as the nanoNAM-derived features (1704 of FIG. 17). The statistical analysis of these 12 microscale features also shows no significance (P value >0.4), as illustrated in the table below.

| Quantitative feature | p-value |
| --- | --- |
| Area | 0.895 |
| Perimeter | 0.864 |
| Roundness | 0.582 |
| Elongation | 0.773 |
| Mean | 0.907 |
| Std (Standard deviation) | 0.526 |
| Skewness | 0.354 |
| Kurtosis | 0.718 |
| Contrast | 0.861 |
| Homogeneity | 0.472 |
| Correlation | 0.823 |
| Uniformity | 0.460 |

Therefore, it was further confirmed that it is indeed the nanoscale sensitivity of nanoNAM that detects early cancer progression, which cannot be identified by both pathologic evaluation and quantitative image features of microscale nuclear architecture.

Discussion

The nanoNAM is a promising approach to address the highly unmet clinical need of personalized risk assessment for patients who are at risk for developing cancer, but not presented with clinically significant lesions. The nanoNAM does not resolve nano-scale structure as super-resolution imaging, but measures the intrinsic nuclear density alteration via nanoscale drOPD at a sensitivity of 1 to 2 nm. The technical advance of nanoNAM enables the analysis of clinical FFPE tissue, the most common form of preserved archived clinical sample, without being compromised by the variation introduced by imperfect clinical sample preparation.

The low-coherence spectral interferometry built into a standard glass slide and closely matched refractive index between the tissue and mounting medium provides the depth-resolved imaging capability to eliminate the variation in tissue thickness. The robust image registration based on high-contrast transmission quantitative phase image allows reliable identification of cell nuclei without being confounded by nuclear staining variation. The use of low coherent light source and a common-path interferometry configuration minimizes multiple noise sources to ensure the reproducibility of nano-scale sensitivity of 1 to 2 nm at a single-nucleus level, crucial for detecting early changes of nuclear architecture in cancer progression in clinical samples, as demonstrated by the extensive validation in animal models and patient samples.

Unlike many biochemistry-based methods, nanoNAM maintains spatial and pathologic context of each cell nucleus, and can serve as an adjunct to pathology. Further, although the cost of nano-NAM will depend on its eventual clinical adoption, a few technical attributes make it potentially low cost. It uses intrinsic scattered light with simple low-NA optics at a clinically feasible throughput (~500 epithelial nuclei in 30 minutes); sample preparation is based on standard low-cost clinical tissue processing (e.g., tissue sectioning, H&E staining) without expensive chemicals.

Although the ability to detect nanoscale changes in cell nucleus has been demonstrated by several other optical imaging techniques, their applicability to assessing cancer progression risk on routine clinical FFPE tissue is limited. Super-resolution fluorescence microscopy (e.g., STORM, PALM, STED) offers good nanoscopic image resolution, but the complex fluorescence staining has a limited performance on clinical FFPE tissue, and their low-throughput and high-cost instrumentation limits their routine clinical use. Other optical techniques such as optical coherence phase microscopy, transmission quantitative phase microscopy, digital holographic microscopy, confocal light absorption and scattering microscopy, and partial-wave spectroscopy can detect structural changes at nanoscale sensitivity using scattered light, but their ability to assess nanoscale nuclear architecture on clinical FFPE tissue can be confounded by either tissue thickness variation, dependence on over-simplified models to interpret optical signals, or lack specificity to cell nuclei; adding nuclear stains affects measured optical signals.

To demonstrate the ability of nanoNAM in detecting early cancer progression, extensive validation was conducted using animal models of colon carcinogenesis and human colitis patients at risk for developing colorectal HGD or adenocarcinoma. By analyzing both histologically normal-appearing cells and pathologically dysplastic cells, gradually denser change of nuclear architecture that correlates with cancer progression was identified, in which the early-stage cancer progression in histologically normal cells prior to dysplasia can be detected by nanoNAM. Demonstrated herein in the clinical utility of nanoNAM to predict "future" colon cancer progression in ulcerative colitis patients with well-documented clinical outcome, by nanoNAM of biopsies obtained at the initial surveillance colonoscopy well before patients developed HGD or adenocarcinoma. The nanoNAM-derived markers, mean positive drOPD (representing denser nuclear architecture alteration) and entropy (representing intranuclear heterogeneity), predict risk of progression with an overall accuracy of 85% (12 of 15 high-risk and 15 of 18 low-risk patients). In comparison, the gold standard (conventional pathology) and digital image analysis using the same set of cell nuclei from each patient did not distinguish high-risk from low-risk patients with statistical significance.

Both pathologic and molecular evidence support the finding that cells undergoing neoplastic transformation accumulate progressive abnormality in nuclear architecture and density distribution that eventually manifest as pathologically detectable characteristics of cancer cells. At the pathologic level, nuclei of cancer cells differ in the amount and distribution of condensed heterochromatin from their normal progenitor cells, which is used for cancer diagnosis and prognosis. At the molecular level, recent studies showed that nuclear architecture with respect to the distribution of condensed and open chromatin regions directly affects mutation rate variation and widespread DNA methylation. A recent electron microscopy study reported an increase in the condensed hetero-chromatin content and clump size in preneoplastic cell nuclei that appear histologically normal, which also suggests the increased density of nuclear architecture in the early-stage cancer development.

Conventional pathology may remain the first-line diagnostic tool. However, the nanoNAM can complement conventional pathology as a cost-effective clinical test to risk-stratify patients for developing cancer, when the cancer progression risk of the patients is unknown. Although this technique is demonstrated in colon carcinogenesis, given that the alteration in nuclear architecture is one of the most universal characteristics in many types of cancer, it may be applicable to other tumor types. As cancer generally develops over a long period of time, the ability to analyze PFFE tissue via the retrospective study allows us to perform our proof-of-concept in patients with accurate clinical phenotype and well-matched low-risk and high-risk group that would otherwise take a decade in a prospective setting. Because progression from ulcerative colitis to adenocarcinoma is very rare, there are only a limited number of high-risk patients that can be identified in a single large medical center. Thus, it has been demonstrated that nanoNAM has a great potential as a cost-effective routine clinical test to predict each at-risk patient's progression risk and personalize their surveillance and treatment strategies to eventually reduce overtreatment and improve early detection of malignancy.

Mathematical Expression of Spectral Interference Signals for drOPD Mapping

For a spatially incoherent source, the detected backscattered wave from the sample may be superimposed with the reference wave reflected at the glass slide-sample interface, resulting in an interference signal:

$$P(k) = S(k)\left[r_r^2 + \int_0^Z r_s^2(z')dz + 2\int_0^Z r_s(z')r_r \cos(2kn(z')z')dz'\right], \quad \text{Equation A}$$

where S(k) is the power spectrum of the source, $r_r$ is the reflection coefficient of the reference wave, $r_s(z)$ is the scattering coefficient of the sample at depth z, Z is the total sample thickness and n(z) is the refractive index profile along the axial z-direction. The Fourier inverse of Equation A results in Equation B:

$$p(z_{opl}) = 2\Gamma \otimes \left[(R_r + R_s)\delta(0) + 2r_r F^{-1}\left(\int_0^Z r_s(z')\cos(2kn(z')z')dz'\right)\right](z_{opl}),$$

Equation B with $$R_r = r_r^2 \text{ and } R_s = \int_0^Z r_s^2(z')dz'.$$

Equation B is a convolution of the source correlation function $\Gamma$ with the interference signal, showing how the source correlation function serves as an implicit coherent window that localizes the information at each optical depth to be within the coherence length. The phase of the Fourier transformed signal at any pre-defined $z_{opl}$ captures nanoscale alterations in OPL at the depth $z_{opl}$, given by Equation C:

$$\delta p(z_{opl}) = \frac{\lambda_0}{2\pi} \angle p(z_{opl}),$$

Equation C where $\lambda_0$ is the center wavelength, $\delta p(z_{opl})$ is the depth-resolved optical path length difference (drOPD) at a specific optical depth location $z_{opl}$, and the phase term $\angle p(z_{opl})$ is determined by Equation D:

$$\angle p(z_{opl}) = \arctan(Im(p(z_{opl})/Re(p(z_{opl}))))$$

Equation D, where Im and Re denote the imaginary and real parts of the complex convolution $p(z_{opl})$. The drOPD is not limited by the axial resolution of optical system, but limited by the system noise.

Equation D describes the phase measurement made at $z_{opl}$ and its physical interpretation given by Equation E:

$$\angle p(z_{opl}) = \arctan\left(\delta z_{opl} \frac{Im(((r'_{opl})^{K_c} \otimes \Gamma)(z_{opl}))}{Re(((r_{opl})^{K_c} \otimes \Gamma)(z_{opl}))}\right),$$

Equation E where $r_{opl} = r_s(z_{opl})$, the actual reflection profile of the scattering object, $r_{opl}'$ is the gradient of the object's reflection profile, and $\Gamma$ is the source correlation function determined by the spectral bandwidth that defines the width of coherent gate, which also determines the axial resolution of the optical system (2 µm in the disclosed aspects). This equation shows that the depth-resolved phase term $\angle p(z_{opl})$ captures the combined effect of two aspects of refractive index profile of the object within the coherence gate. The first term of Equation E, given by $\delta z_{opl}$, is the sub-resolution offset that measures the sub-resolution deviation between the optical depth $z_{opl}$ where the phase measurement is made, and the optical depth corresponding to the weighted-center of the coherence-gated refractive index profile of the object around the optical depth $z_{opl}$ being probed. This deviation exists because the weighted-center, due to alteration in the refractive index profile of the object within the coherent gate centered at $z_{opl}$, can be different from $z_{opl}$. $\delta z_{opl}$ allows the estimation of this difference. The second term of Equation E, given by the fraction, is an estimate of the average rate-of-change of the refractive index profile (or mean spatial-frequency) within the coherence gate at the optical depth being probed. This can be understood by observing that the imaginary part in the numerator—integration (written as a convolution, $\otimes$, with $\Gamma$) of the baseband representation (indicated by the superscript $K_c$, the center frequency of the source) of $r_{opl}'$ within the coherence gate—is a measure of the mean gradient of refractive index profile within the coherence gate, while the real part of the denominator—integration of the baseband representation of $r_{opl}$ within the coherence gate—measures the net change in the refractive index profile within the coherence gate. Together, their ratio estimates the average rate-of-change, or mean spatial-frequency, of the coherence-gated refractive index profile. It is noted that the imaginary and real parts of the numerator and denominator respectively make the representation consistent with the arctangent for phase representation. When the coherent gate is moved along the axial direction with a step size much smaller than the width of the coherence gate (0.045 µm according to an aspect), the drOPD captures the gradual change of the refractive index profile along the axial direction. When drOPD is averaged over a certain optical-depth range, the effect of sub-resolution offset, $\delta z_{opl}$, the first term of Equation E, is cancelled out such that the average drOPD primarily captures the effect of the rate-of-change (mean spatial-frequency) of the coherence-gated refractive index profile. Therefore, the drOPD quantifies the changing (increasing or decreasing) optical density within the gate, and its mean heterogeneity.

Numerical Simulation to Illustrate Depth-Resolved drOPD Imaging

Figure 19:
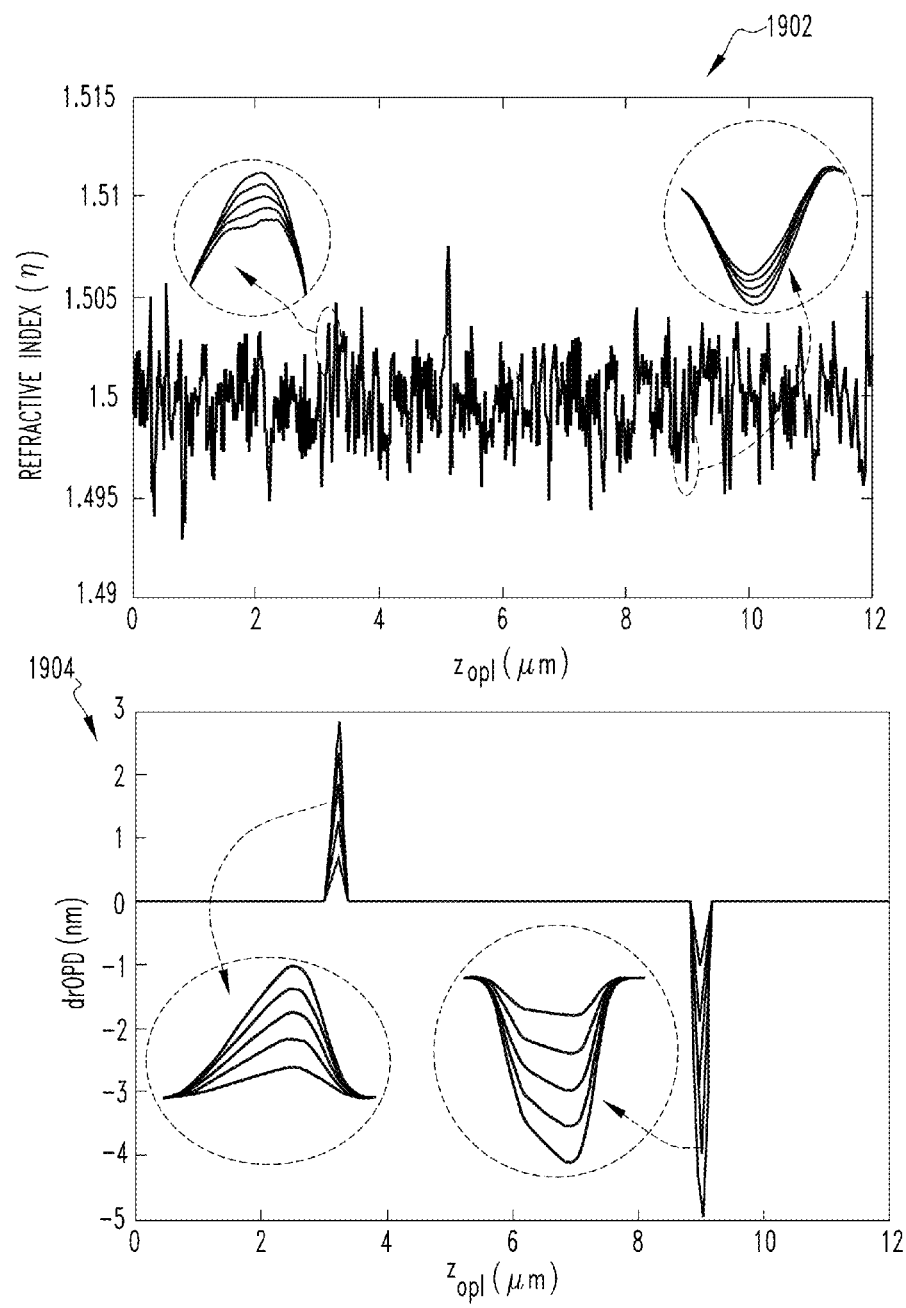
FIG. 19 illustrates the concept of depth-resolved imaging with numerical simulation.

FIG. 19 illustrates the concept of depth-resolved imaging with numerical simulation. To perform the numerical simulation, consider a low-coherence spectral source with same spectral bandwidth as the experimental light source. A Gaussian random process based refractive index profile is generated with the step size of 1 nm (illustrated at 1902). A wave transfer matrix is used to implement wave propagation and reflection through the refractive index profile. For each wavelength, the back-reflected waves from all depths are interfered with a reference wave to generate the spectral interference signal. The self-interference of the reference and back-reflected sample waves are ignored.

After normalizing by the shape of the source spectrum, the Fourier transform of the spectral interference is performed and its phase as a function of optical depth is computed using Equation A. The phase is unwrapped and the phase ramp due to the center frequency (corresponding to the center wavelength) of the light source is subtracted from it. The gradient of the resulting phase is calculated.

To obtain $\angle p(z_{opl})$ at a particular optical depth of interest, the phase gradient is integrated within the coherence gating around that optical depth. Finally $\delta p(z_{opl})$ is computed by multiplying $\angle p(z_{opl})$ by $$\frac{\lambda_0}{2\pi}.$$

As shown at 1902, the structure of the scattering object is described by the refractive index profile along the optical depth, which does not have any strong interface, mimicking the internal architecture of cell nucleus.

A local structural change is represented by a small increase of refractive index (or increased rate-of-change) at Location 1 and the corresponding decreased refractive index change at Location 2, as shown in the figure insets at 1902. The phase profile of Fourier transform of spectral interference signal captures the local sub-resolution change of refractive index at their respective optical depth centered around the coherent gate, as shown at 1904.

Figure 20:
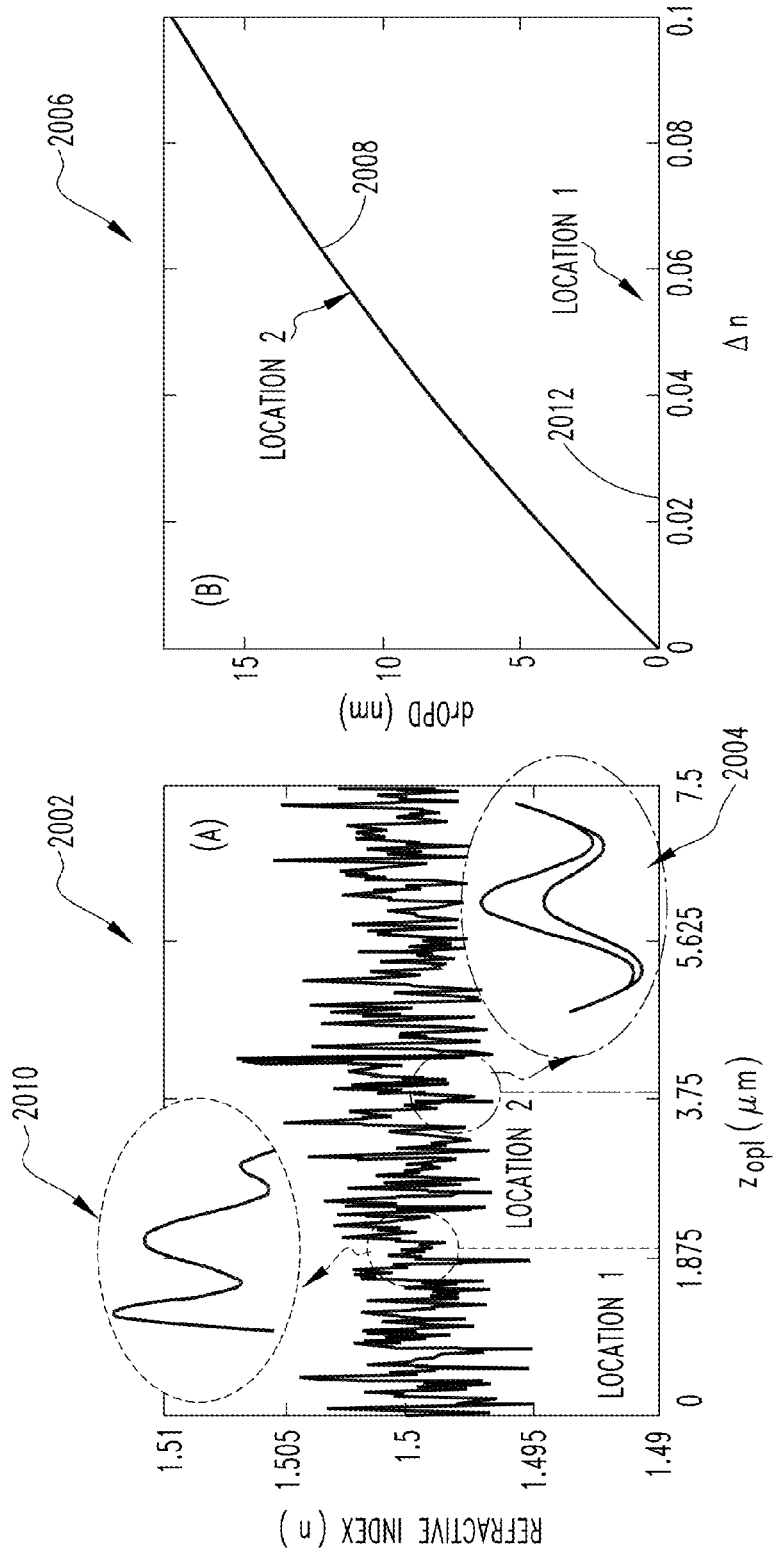
FIG. 20 illustrates the effect of changing refractive index of the scattering object on depth resolved optical path-length difference.

Increasing local refractive index (or rate-of-change of refractive index) leads to positive drOPD. It should be noted that such internal structural changes cannot be detected by conventional transmission phase imaging, as the accumulative phase along the entire sample depth remains constant. The drOPD value goes up with increasing refractive index (as illustrated in FIG. 20). This result shows the ability of drOPD to detect minute local change in refractive index profile at a specific depth.

FIG. 20 illustrates the effect of changing refractive index of the scattering object on drOPD. At 2002 is a refractive index profile of an object with a local change of refractive index at Location 2, indicated by circle 2004 (Location 2). As illustrated at 2006, the drOPD value at Location 2 (curve 2008) increases when the local refractive index goes up. At substantially the same time, the drOPD remains the same at Location 1 (circle 2010) where there is no change in the refractive index profile indicated by curve 2012.

Depth-Resolved Imaging Via drOPD

To experimentally confirm the depth-resolved imaging capability, an unstained slide from a thin section (5 μm) of a cell block containing HeLa cells embedded in a polymer network of HistoGel® was used. FIG. 21 illustrates a demonstration of depth-resolved capability of drOPD imaging. At 2102 is a bright-field image and, at 2104, is a transmission quantitative phase map of a 5 μm section of cell block. Elements 2106-2110 are the corresponding drOPD maps of the cell section at optical depth ($Z_{OPL}$) of 1 μm (at 2106), 2 μm (at 2108), and 5 μm (at 2120). The color bar represents nanometer.

As 2102, the bright-field image of cell section shows cells embedded in polymer network. Its quantitative phase map obtained from transmission diffraction phase microscope) is shown at 2104, in which the accumulative phase (or optical path length (OPL)) for light passing through the entire sample is measured.

As indicated, at 2106-2110 are illustrated the corresponding drOPD maps at three optical depths ($z_{opl}$=1, 2, and 5 μm). At a superficial optical depth of 1 μm (at 2106), the drOPD map shows both cells and polymer network. At an optical depth of 2 μm (at 2108), the polymer network is barely visible, indicating the depth sectioning capability of drOPD mapping. At a deeper depth of 5 μm (at 2110), the polymer network becomes invisible.

The cell, indicated by circle 2112, is visible at 1 and 2 μm, but disappears at 5 μm; while the cell, indicated by circle 2114, can be seen in all three depths, indicating the thickness variation of different cells (thicker cell, indicated by circle 2114, than the cell, indicated by circle 2112). This thickness difference is further supported by transmission quantitative phase map (illustrated at 2104), in which the cell, indicated by circle 2114, shows a higher optical pathlength (OPL) than the cell, indicated by circle 2112.

Although both transmission phase map and drOPD map measure phase changes, this result highlights the complementary nature of these two approaches: drOPD map can detect internal cell structural characteristics independent of cell thickness, but has a low image contrast; while transmission phase map measures the integrated OPL along the entire sample depth that is sensitive to thickness, but provides a high image contrast. In both methods, the unstained image does not provide sufficient contrast to unambiguously identify cell nuclei, suggesting the need for a different contrast mechanism.

Cell Block Processing

Cell block used in FIG. 21 was processed in the Tissue and Research Pathology Service at University of Pittsburgh. In brief, cells fixed in 4% formalin were first concentrated by spinning cells in a centrifuge tube until a cell pellet was formed. Then the HistoGel (Thermo Scientific) was added to the cell pellet. After the histogel embedded with cell pellet solidifies, 4% formalin was added to remove the cell block (gel button with specimen cells) from the container. The cell pellet was then embedded in embedded in paraffin, as a paraffin-embedded cell block. Each slide from the cell block was prepared following the same standard tissue histology processing protocol except no staining used: the paraffin block was sectioned at 5 μm thickness; and a cell section was placed on the glass slide, then paraffin was removed, and coverslipped with the mounting medium (Micromount®, n=1.50, Surgipath, Leica).

CONCLUSION

The various aspects discussed herein provide systems, apparatuses, and methods to predict cancer progression risk via nanoscale nuclear architecture mapping (nanoNAM) of unstained tissue sections based on the intrinsic density alteration of nuclear structure rather than the amount of stain uptake. It has been demonstrated that nanoNAM detects a gradual increase in the density alteration of nuclear architecture during malignant transformation in animal models of colon carcinogenesis and in human patients with ulcerative colitis, even in tissue that appears histologically normal according to pathologists. The ability of nanoNAM to predict "future" cancer progression in patients with ulcerative colitis who did and did not develop colon cancer up to 13 years after their initial colonoscopy was evaluated. NanoNAM of the initial biopsies correctly classified 12 of 15 patients who eventually developed colon cancer and 15 of 18 who did not, with an overall accuracy of 85%. Taken together, these findings demonstrate great potential for nanoNAM in predicting cancer progression risk and suggest that further validation in a multicenter study with larger cohorts may eventually advance this method to become a routine clinical test.

Although the subject matter has been described in language specific to structural features or methodological acts, it is to be understood that the subject matter of the appended claims is not necessarily limited to the specific features or acts described above. Rather, the specific features and acts described above are disclosed as example embodiments.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or." Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first," "second," or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel. Additionally, "comprising," "comprises," "including," "includes," or the like generally means comprising or including.

Although the disclosure has been shown and described with respect to one or more implementations, equivalent alterations and modifications will occur based on a reading and understanding of this specification and the annexed drawings. The disclosure includes all such modifications and alterations and is limited only by the scope of the following claims.

What is claimed is:

1. A spatial-domain low-coherence quantitative phase microscopy apparatus, comprising:
   an imaging system that collimates a white light from a light source;
   a component that tunes a wavelength of the white light to a spectral resolution shared by multiple imaging contrasts;
   a device that projects the tuned light onto a sample, wherein the sample scatters at least a portion of the tuned light back;
   a camera that records the scattered portion of the tuned light and generates a depth-resolved three-dimensional image based, at least in part, on a measurement of the scattered portion; and
   an image registration module that is configured to co-registers the depth-resolved three-dimensional image with a bright field image of a stained version of the sample using coordinate transformation information generated from an unstained transmission phase image of the sample and a stained transmission phase image of the stained version of the sample.

2. The apparatus of claim 1, wherein first nuclei locations are identified in the bright field image of the stained version of the sample, and wherein the image registration module is configured to identify second nuclei locations in the depth-resolved three-dimensional image using the first nuclei locations and the coordinate transformation information.

3. The apparatus of claim 1, wherein the image registration module is configured to generate the coordinate transformation information by individually thresholding the unstained transmission phase image of the sample and the stained transmission phase image of the stained version of the sample.

4. The apparatus of claim 1, wherein the individually thresholding comprises identifying respective landmark features in each of the unstained transmission phase image of the sample and the stained transmission phase image of the stained version of the sample.

5. The apparatus of claim 4, wherein the coordinate transformation information is based on a normalized cross-correlation between the respective landmark features of the unstained transmission phase image of the sample and the stained transmission phase image of the stained version of the sample.

6. The apparatus of claim 5, wherein the coordinate transformation information includes scaling and rotation information.

7. A spatial-domain low-coherence quantitative phase microscopy method, comprising:
   tuning a wavelength of a white light;
   projecting the tuned light onto a sample, wherein the sample scatters at least a portion of the tuned light back;
   recording the scattered portion of the tuned light with a camera;
   generating a depth-resolved three-dimensional image based, at least in part, on a measurement of the scattered portion;
   and
   co-registering the depth-resolved three-dimensional image with a bright field image of a stained version of the sample using coordinate transformation information generated from an unstained transmission phase image of the sample and a stained transmission phase image of the stained version of the sample.

8. The method of claim 7, wherein first nuclei locations are identified in the bright field image of the stained version of the sample, and wherein the co-registering comprises identifying second nuclei locations in the depth-resolved three-dimensional image using the first nuclei locations and the coordinate transformation information.

9. The method of claim 7, wherein the co-registering comprises identifying respective nuclei locations in the depth-resolved three-dimensional image.

10. The method of claim 7, wherein the coordinate transformation information is generated by individually thresholding the unstained transmission phase image of the sample and the stained transmission phase image of the stained version of the sample.

11. The method of claim 10, wherein the individually thresholding comprises identifying respective landmark features in each of the unstained transmission phase image of the sample and the stained transmission phase image of the stained version of the sample.

12. The method of claim 11, wherein the coordinate transformation information is based on a normalized cross-correlation between respective landmark features of the unstained transmission phase image of the sample and the stained transmission phase image of the stained version of the sample.

13. The method of claim 12, wherein the coordinate transformation information includes scaling and rotation information.

14. The method of claim 7, further comprising covering the sample by a glass slide, wherein one face of the glass slide is covered by a reflection-enhancing coating.

15. The method of claim 7, further comprising directing light to the sample.

16. The method of claim 15, the method further comprising projecting a reflected reference wave and backscattered light from the sample to the camera.

17. The method of claim 16, wherein a diffracted beam is collected at the camera.

18. The method of claim 15, the method further comprising performing trans-illumination for transmission phase imaging based on a configuration of a diffraction phase microscope.

19. The method of claim 7, wherein the depth-resolved three-dimensional image is auto-focused based, at least in part, on a fixed wavelength.

* * * * *